(12) United States Patent
Argentine et al.

(10) Patent No.: US 12,370,037 B2
(45) Date of Patent: *Jul. 29, 2025

(54) STENT-GRAFT PROSTHESIS WITH PRESSURE RELIEF CHANNELS

(71) Applicant: Medtronic Vascular, Inc., Santa Rosa, CA (US)

(72) Inventors: Jeffery Argentine, Petaluma, CA (US); Mitchell Springer, Santa Rosa, CA (US); Adam Shipley, San Rafael, CA (US); Mark Stiger, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 17/703,562

(22) Filed: Mar. 24, 2022

(65) Prior Publication Data

US 2022/0211484 A1 Jul. 7, 2022

Related U.S. Application Data

(63) Continuation of application No. 15/960,622, filed on Apr. 24, 2018, now Pat. No. 11,284,989.

(51) Int. Cl.
*A61F 2/07* (2013.01)
*A61F 2/24* (2006.01)

(52) U.S. Cl.
CPC .............. *A61F 2/07* (2013.01); *A61F 2/2476* (2020.05); *A61F 2210/0014* (2013.01);
(Continued)

(58) Field of Classification Search
CPC ...... A61F 2/07; A61F 2/95; A61F 2250/0013; A61F 2250/0069; A61F 2/2476; A61F 2002/077
See application file for complete search history.

(56) References Cited

U.S. PATENT DOCUMENTS 6,398,803 B1 6/2002 Layne et al.
6,645,242 B1 11/2003 Quinn
(Continued)

FOREIGN PATENT DOCUMENTS

CN 102076285 A 5/2011
EP 2740439 A1 7/2014
(Continued)

OTHER PUBLICATIONS

EP Appln. No. 19169027.0, Extended EP Search Report, Aug. 22, 2019, 8 pages.
(Continued)

*Primary Examiner* — Brian E Pellegrino
(74) *Attorney, Agent, or Firm* — Medler Ferro Woodhouse & Mills PLLC

(57) ABSTRACT

A stent-graft prosthesis for implantation within a body vessel includes a graft material, a frame, and a channel. The graft material includes a proximal end, a distal end, and a graft lumen extending between the proximal and distal ends. The frame is coupled to the graft material. The channel is configured to relieve pressure associated with pulsatile blood flow during implantation of the stent-graft prosthesis within a body vessel. The channel permits blood to flow from an upstream side of the stent-graft prosthesis to a downstream side of the stent-graft prosthesis when the stent-graft prosthesis is in a partially expanded configuration in the body vessel. The channel may be a plurality of channels.

9 Claims, 22 Drawing Sheets

(52) U.S. Cl.
CPC ............... *A61F 2230/0023* (2013.01); *A61F 2250/0013* (2013.01); *A61F 2250/0069* (2013.01)

(56) References Cited

U.S. PATENT DOCUMENTS

| | | | |
|---|---|---|---|
| 7,955,373 | B2 | 6/2011 | Sowinski et al. |
| 8,882,828 | B2 | 11/2014 | Kinkade et al. |
| 8,992,593 | B2 | 3/2015 | Chuter et al. |
| 9,498,323 | B2 | 11/2016 | King |
| 9,566,149 | B2 | 2/2017 | Shaw |
| 10,105,250 | B2 | 10/2018 | Berra |
| 10,159,558 | B2 | 12/2018 | Chuter et al. |
| 11,284,989 | B2 * | 3/2022 | Argentine ............... A61F 2/07 623/1.13 |
| 11,357,612 | B2 | 6/2022 | Shipley et al. |
| 2001/0032009 | A1 | 10/2001 | Layne et al. |
| 2006/0100694 | A1 | 5/2006 | Globerman |
| 2006/0184089 | A1 | 8/2006 | Makower et al. |
| 2008/0109066 | A1 | 5/2008 | Quinn et al. |
| 2009/0276027 | A1 | 11/2009 | Glynn |
| 2010/0204784 | A1 | 8/2010 | Molaei et al. |
| 2011/0160833 | A1 | 6/2011 | Gonzalez et al. |
| 2011/0178590 | A1 | 7/2011 | Zucker |
| 2011/0270378 | A1 | 11/2011 | Bruszewski et al. |
| 2012/0130478 | A1 | 5/2012 | Shaw |
| 2012/0290069 | A1 | 5/2012 | Ivancev et al. |
| 2012/0179235 | A1 | 7/2012 | Lazarus et al. |
| 2012/0221094 | A1 | 8/2012 | Cunningham et al. |
| 2012/0296406 | A1 | 11/2012 | Minion |
| 2013/0172984 | A1 | 7/2013 | Greenberg et al. |
| 2014/0014888 | A1 | 1/2014 | Lung |
| 2015/0012080 | A1 | 1/2015 | Barrand |
| 2015/0216684 | A1 | 8/2015 | Enzmann et al. |
| 2016/0310216 | A1 | 10/2016 | Van Bibber et al. |
| 2016/0324670 | A1 | 11/2016 | Yamaguchi |
| 2017/0056215 | A1 | 3/2017 | Nagesh et al. |
| 2017/0281331 | A1 | 10/2017 | Perkins et al. |
| 2018/0303641 | A1 | 10/2018 | Roeder et al. |

FOREIGN PATENT DOCUMENTS

| | | | | |
|---|---|---|---|---|
| EP | 3053545 | B1 | 9/2019 | |
| EP | 3342372 | B1 | 9/2020 | |
| EP | 2564811 | B1 | 3/2021 | |
| WO | 20110076408 | A1 | 6/2011 | |
| WO | WO-2013055293 | A1 * | 4/2013 | ............ A61F 2/856 |
| WO | 2013/162682 | A1 | 10/2013 | |
| WO | 20170137868 | A1 | 8/2017 | |

OTHER PUBLICATIONS

Communication Pursuant to Article 94(3), EP Application No. 19 169 027.0, 7 pages.

Extended European Search Report, EP Application No. 22156798.5, dated Jul. 27, 2022, 8 pages.

* cited by examiner

STENT-GRAFT PROSTHESIS WITH PRESSURE RELIEF CHANNELS

CROSS-REFERENCE TO RELATED APPLICATIONS

This application is a continuation of U.S. patent application Ser. No. 15/960,622, filed Apr. 24, 2018, the contents of which are incorporated by reference herein in their entirety.

FIELD OF THE INVENTION

The present invention generally relates to stent-graft prostheses having pressure relief channels.

BACKGROUND OF THE INVENTION

Stent-graft prostheses are prostheses for percutaneous implantation in blood vessels or other similar organs of the living body. These stent-graft prostheses typically include one or more radially compressible stents that can be expanded within the body vessel at a diameter slightly larger than the body vessel, and a graft material interior or exterior of the stent. When the stent-graft prosthesis is radially expanded in situ, the one or more stents anchor the tubular graft material to the wall of a blood vessel or anatomical conduit. Thus, stent-graft prostheses are typically held in place by mechanical engagement and friction due to the opposition forces provided by the radially expanded stents against the vessel wall. When the one or more stents are expanded, the graft material is anchored on the interior wall of the body vessel. Thus, the graft material is held in place by the friction between the one or more stents and the body vessel.

Stent-graft prostheses are often utilized for treating aneurysms, dissections and transections. In an example, an aneurysm may result from weak, thinned blood vessel walls that "balloon" or expand due to aging, disease and/or blood pressure in the vessel. These aneurysmal blood vessels have a potential to rupture, causing internal bleeding and potentially life threatening conditions. When the stent-graft prosthesis is implanted within an aneurysmal blood vessel, with the stent-graft prosthesis extending proximal and distal of the aneurysm, the stent-graft prosthesis acts as a bypass lumen that permits blood to flow through the graft material instead of the expanded section of the aneurysm. Stent-graft prostheses, therefore, isolate aneurysms or other blood vessel abnormalities from normal blood pressure, reducing pressure on the weakened vessel wall and reducing the chance of vessel rupture.

Stent-graft prostheses may have an open-web configuration or a closed-web configuration. In an open-web configuration, the end of the frame (stent(s)) of the stent-graft prosthesis extends beyond a corresponding end of the graft material, and thus has a portion that is not covered by the graft material. The uncovered portion generally permits blood flow through the stent-graft prosthesis during implantation. The uncovered portion of the open-web configuration further provides a convenient location for coupling to a tip-capture mechanism of a delivery catheter. However, with the uncovered portion of the frame gathered tightly by the tip-capture mechanism, flow through the uncovered portion is not always ideal. In the closed-web configuration, the end of the frame (stent(s)) of the stent-graft prosthesis is covered or lined by the graft material. Thus, the closed-web configuration has no exposed stents and is intended to reduce potential trauma between the stent-graft prosthesis and the vessel. For example, stent-graft prostheses having a closed-web configuration may be selected to treat aneurysms, dissections or vessel transections due to the delicate condition of the vessel tissue. A closed-web configuration stent-graft prosthesis thus is less traumatic to sensitive tissues and disease states. A closed-web configuration stent-graft prosthesis offers convenience by preserving the structural integrity of fragile blood vessel tissues.

For implantation within a blood vessel, the stent-graft prosthesis is deployed through a minimally invasive intraluminal delivery procedure. More particularly, a body lumen or vasculature is accessed percutaneously at a convenient entry point, such as a femoral artery, and the stent-graft prosthesis is routed through the vasculature to the desired treatment location. For example, a self-expanding stent-graft prosthesis may be compressed and disposed within a distal end of an outer shaft or sheath component of a delivery catheter as part of a delivery system. A proximal or upstream end of the stent-graft prosthesis is removably coupled to a tip capture mechanism of an inner shaft or member. The delivery system is then maneuvered, typically tracked through a body lumen until a distal end of the delivery system and the stent-graft prosthesis are positioned at the intended treatment site. The outer sheath of the delivery system is withdrawn. The tip capture mechanism prevents the stent-graft prosthesis from being withdrawn with the outer sheath, and further prevents the proximal or upstream end of the stent-graft prosthesis from fully expanding. As the outer sheath is withdrawn, the stent-graft prosthesis is released from the confines thereof and a distal portion of the stent-graft prosthesis radially expands to contact and substantially conforms to a portion of the surrounding interior of the body lumen, e.g., the blood vessel wall. When the stent-graft prosthesis is in the desired positon, the tip capture mechanism is actuated. As the tip capture mechanism is actuated, the proximal or upstream end of the stent-graft prosthesis radially expands to transition the stent-graft prosthesis to a radially expanded configuration.

However, when the stent-graft prosthesis is partially expanded against the vessel wall, but the proximal (upstream) end of the stent-graft prosthesis is captured by the tip capture mechanism, there is nowhere for the blood to flow past the stent-graft prosthesis. Thus, pulsatile blood pressure against the proximal or upstream end of the stent-graft prosthesis may cause the stent-graft prosthesis to move during deployment, thereby presenting challenges in accurately positioning and deploying the stent-graft prosthesis. Further, blood does not flow to vessels downstream of the stent-graft prosthesis, thereby risking injury due to ischemia. Further, in some methods in which the upstream end of the stent-graft prosthesis is deployed first and the downstream end of the stent-graft prosthesis remains captured by the delivery system, blood flow entering the stent-graft prosthesis at the upstream end cannot escape the stent-graft prosthesis, thereby depriving blood flow distal of the stent-graft prosthesis.

Accordingly, there is a need for stent-graft prostheses providing blood flow during deployment thereof for improved positioning and deployment accuracy, and to maintain blood flow to vessels distal of the stent-graft prosthesis.

BRIEF SUMMARY OF THE INVENTION

Embodiments hereof relate to a stent-graft prosthesis for implantation within a body vessel. The stent-graft prosthesis includes a graft material, a frame, and a channel. The graft material includes a first end, a second end, and a graft lumen extending between the first and the second end. The frame is coupled to the graft material. The channel of the stent-graft prosthesis is configured for relieving pressure associated with pulsatile blood flow during implantation of the stent-graft prosthesis within a body vessel. The channel of the stent-graft prosthesis permits blood to flow from an upstream side of the stent-graft prosthesis to a downstream side of the stent-graft prosthesis when the stent-graft prosthesis is in a partially expanded configuration in the body vessel.

Embodiments hereof also relate to a stent-graft prosthesis for implantation within a body vessel. The stent-graft prosthesis includes a graft material, a frame, and a channel. The graft material includes a first end, a second end, and a graft lumen extending between the first and the second end. The frame is coupled to the graft material. The channel of the stent-graft prosthesis is configured to relieve pressure associated with pulsatile blood flow during implantation of the stent-graft prosthesis within a body vessel. The channel of the stent-graft prosthesis permits blood to flow from an upstream side of the stent-graft prosthesis to a downstream side of the stent-graft prosthesis when the stent-graft prosthesis is in a partially expanded configuration in the body vessel. The channel includes a channel lumen extending from a channel entrance to a channel exit. The channel lumen is a portion of the graft lumen. The channel entrance is disposed through the graft material and is configured to permit blood flow to the channel lumen when the stent-graft prosthesis is in the partially expanded configuration. The channel exit is disposed through the graft material distal of the channel entrance and is configured to permit blood flow from the channel lumen when the stent-graft prosthesis is in the partially expanded configuration.

Embodiments hereof further relate to a stent-graft prosthesis for implantation within a body vessel. The stent-graft prosthesis includes a graft material, a frame, and a channel. The graft material includes a first end, a second end, and a graft lumen extending between the first and the second end. The frame is coupled to the graft material. The frame includes at least one body stent. The channel of the stent-graft prosthesis is configured to relieve pressure associated with pulsatile blood flow during implantation of the stent-graft prosthesis within a body vessel. The channel is defined between the outer surface of the graft material and an adjacent first segment of the at least one body stent to which the graft material is not attached in the radially expanded state when the stent-graft prosthesis is in the partially expanded configuration. The channel of the stent-graft prosthesis is configured to permit blood to flow from an upstream side of the stent-graft prosthesis to a downstream side of the stent-graft prosthesis when the stent-graft prosthesis is in a partially expanded configuration in the body vessel.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
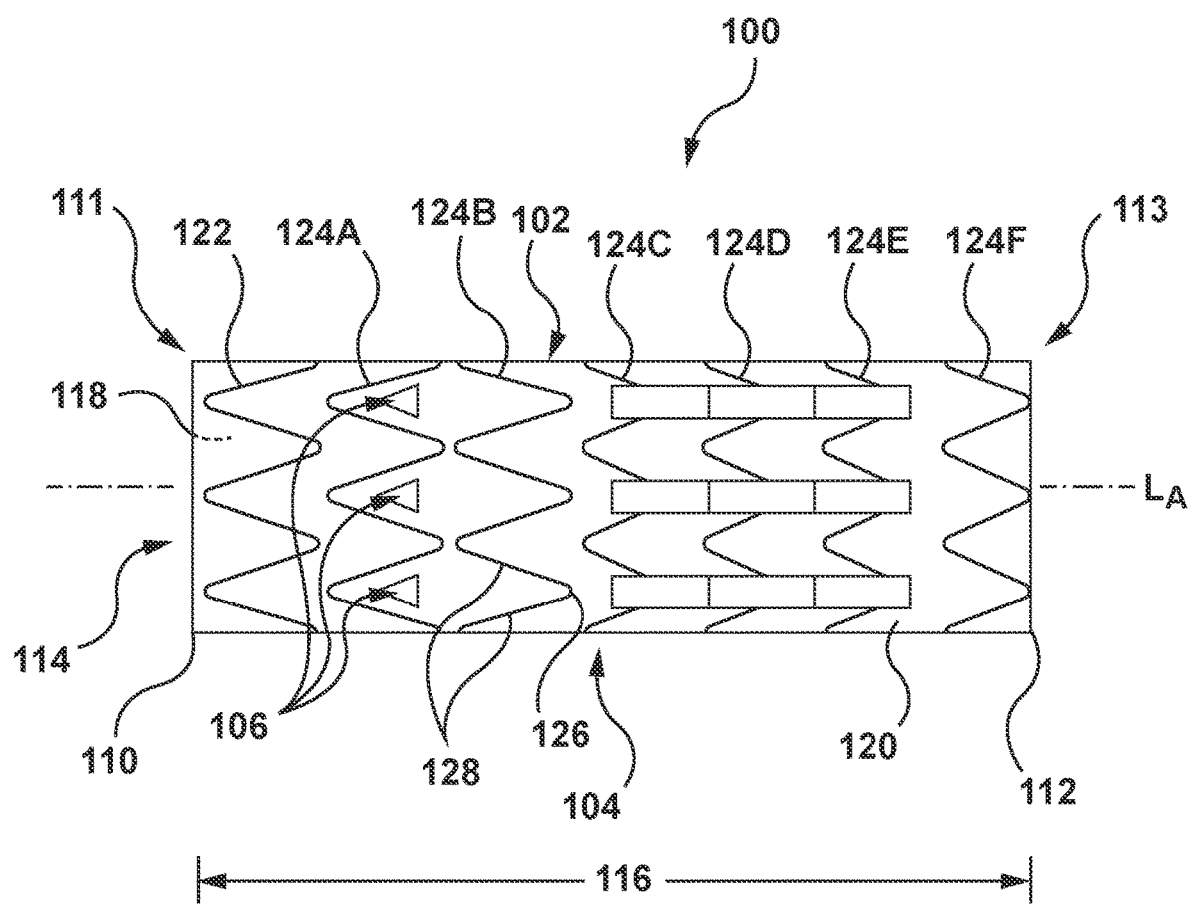
FIG. 1 depicts a side view of a stent-graft prosthesis having channels for relieving pulsatile blood pressure according to an embodiment hereof, wherein the stent-graft prosthesis is in a radially expanded configuration.

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel or a device to be implanted into a native vessel, such as a stent-graft prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

In addition, the term "self-expanding" is used in the following description with reference to one or more stent structures of the stent-graft prosthesis, and is intended to convey that the structures are shaped or formed from a material that can be provided with a mechanical memory to return the structure from a radially compressed or collapsed configuration to a radially expanded configuration. Non-exhaustive exemplary self-expanding materials include stainless steel, a pseudo-elastic metal such as a nickel titanium alloy (e.g. NITINOL), various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy (e.g. NITINOL).

The following detailed description is not intended to limit the invention or the application and uses of the invention. Although the description of the invention is in the context of the treatment of blood vessels such as the aorta, the invention may also be used in any other body passageways where it is deemed useful, non-limiting examples of which include coronary arteries, carotid arteries, and renal arteries. Therefore, the term body vessel, or vessel, is used to apply to the body passageways as a whole. Furthermore, there is no intention to be bound by any expressed or implied theory presented in the preceding technical field, background, brief summary or the following detailed description.

A stent-graft prosthesis in accordance with embodiments hereof includes at least one channel configured to relieve pulsatile blood pressure at a first, proximal or upstream end of the stent-graft prosthesis when the stent-graft prosthesis is in a partially expanded configuration. As will be explained in more detail below, the stent-graft prosthesis includes at least one channel configured to permit blood flow from upstream of the stent-graft prosthesis to downstream of the stent-graft prosthesis as the stent-graft prosthesis is transitioning from a radially compressed configuration for delivery to a radially expanded configuration when deployed.

FIGS. 1-12 illustrate a stent-graft prosthesis 100 according to an embodiment hereof. As shown in FIG. 1, the stent-graft prosthesis 100 includes a graft material 102, a frame 104, and channels 106. The stent-graft prosthesis 100 has a radially compressed configuration for delivery, a radially expanded configuration when deployed, and a partially expanded configuration when transitioning between the radially compressed and the radially expanded configurations. When the stent-graft prosthesis 100 is in the radially expanded configuration at a desired treatment location, the stent-graft prosthesis 100 is configured to bypass a vessel abnormality such as an aneurysm within a body vessel. While described herein as configured to bypass an aneurysm, such as an abdominal aortic aneurysm, this is by way of example and not limitation, and the stent-graft prosthesis 100 may be configured to support/bypass other vessel abnormalities such as, but not limited to dissections and transections.

The graft material 102 is of a generally tubular shape having a central longitudinal axis $L_A$, a first end or edge 110, a second end or edge 112, and a graft lumen 114 extending from the first end 110 to the second end 112. The graft material 102 has a longitudinal length 116, which may vary based upon the application. The graft material 102 further includes an inner surface 118 and an outer surface 120. The first end 110 of the graft material 102 may be referred to as a proximal or an upstream end or edge of the graft material 102. In the embodiment shown, the first end 110 of the graft material is also a first, proximal or upstream end or edge 111 of the stent-graft prosthesis 100. The second end 112 of the graft material 102 may be referred to as a distal or a downstream end or edge of the graft material 102. In the embodiment shown, the second end 112 of the graft material 102 is also a second, distal, or downstream end or edge 113 of the stent-graft prosthesis 100. For a stent-graft prosthesis for an abdominal aortic aneurysm delivered from the femoral artery, the proximal or upstream end 111 of the stent-graft prosthesis 100 is the end that is coupled to a tip capture mechanism of a delivery system. The graft material 102 may be formed from any suitable graft material, for example and not way of limitation, the graft material 102 may be formed from a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

In the embodiment of FIGS. 1-12, the frame 104 of the stent-graft prosthesis 100 includes a sealing or seal stent 122 and at least one body stent 124. The frame 104 is configured to support the graft material 102. The seal stent 122 and each of the body stents 124 of the frame 104 are coupled to the graft material 102. In the embodiment illustrated in FIG. 1, the stent-graft prosthesis 100 is shown in the radially expanded configuration and includes one (1) seal stent 122 adjacent to the first end 110, and six (6) body stents 124A, 124B, 124C, 124D, 124E, and 124F axially or longitudinally spaced between the first end 110 and the second end 112 of the graft material 102. Although shown with six (6) body stents 124, it will be understood that the stent-graft prosthesis 100 may include a greater or smaller number of body stents 124 depending upon the desired length 116 of the stent-graft prosthesis 100 and/or the intended application. The seal stent 122 and each of the body stents 124 are self-expanding and each includes a radially compressed state, a partially expanded state, and a radially expanded state. Accordingly, the seal stent 122 and each of the body stents 124 are constructed from self-expanding materials as described previously. The seal stent 122 and each of the body stents 124 may be sinusoidal patterned rings including a plurality of crowns or bends 126 and a plurality of struts or straight segments 128 with each crown 126 being formed between a pair of adjacent struts 128. While the seal stent 122 and the body stents 124 are shown in FIG. 1 as having a similar sinusoidal pattern, it will be understood that the seal stent 122 and the body stents 124 may have different patterns or configurations. The seal stent 122 and the body stents 124 are coupled to the graft material 102 by stitches, sutures, or other suitable methods. In the embodiment of FIG. 1, the seal stent 122 and the body stents 124 are coupled to the outer surface 120 of the graft material 102. However, the seal stent 122 and the body stents 124 may each alternatively be coupled to the inner surface 118 of the graft material 102. When the stent-graft prosthesis 100 is used for treating an aneurysm, the seal stent 122 is configured with sufficient radial spring force and flexibility to conformingly engage the stent-graft prosthesis 100 with the body lumen inner wall, to avoid excessive leakage, and to prevent pressurization of the aneurysm, i.e., to provide a leak-resistant seal.

Figure 2:
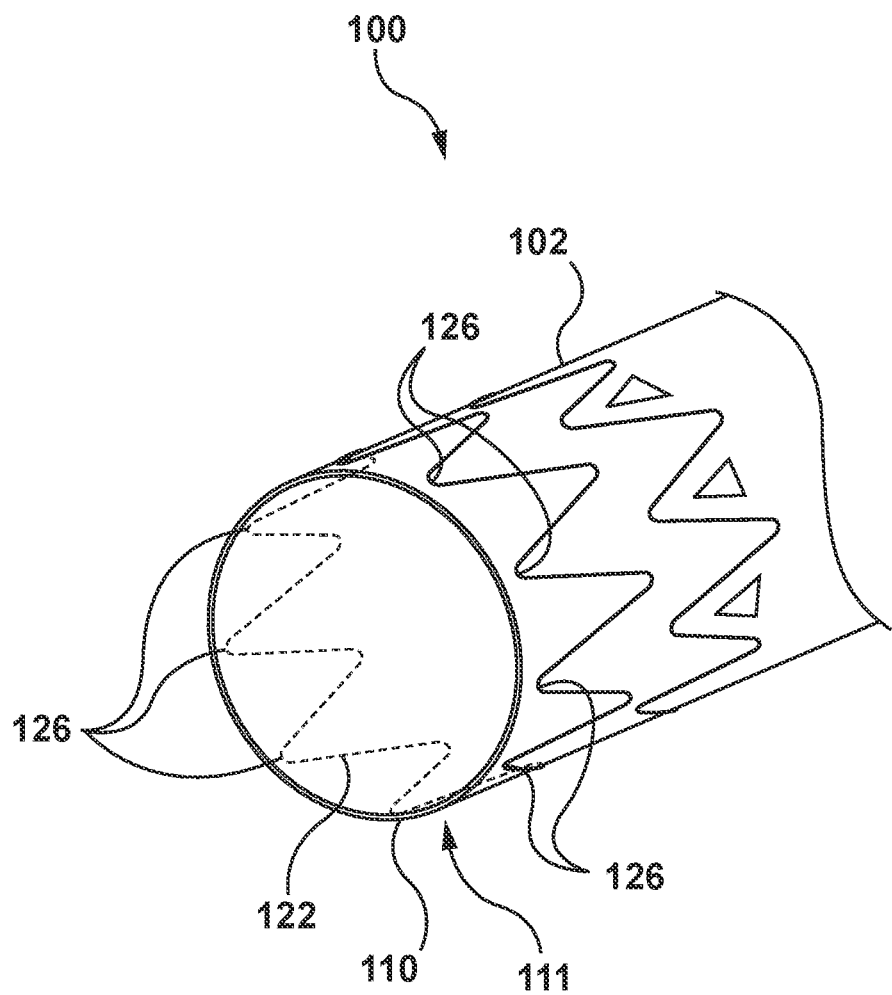
FIG. 2 depicts a perspective view of a first end of the stent-graft prosthesis of FIG. 1, wherein the stent-graft prosthesis is in the radially expanded configuration.
Figure 3:
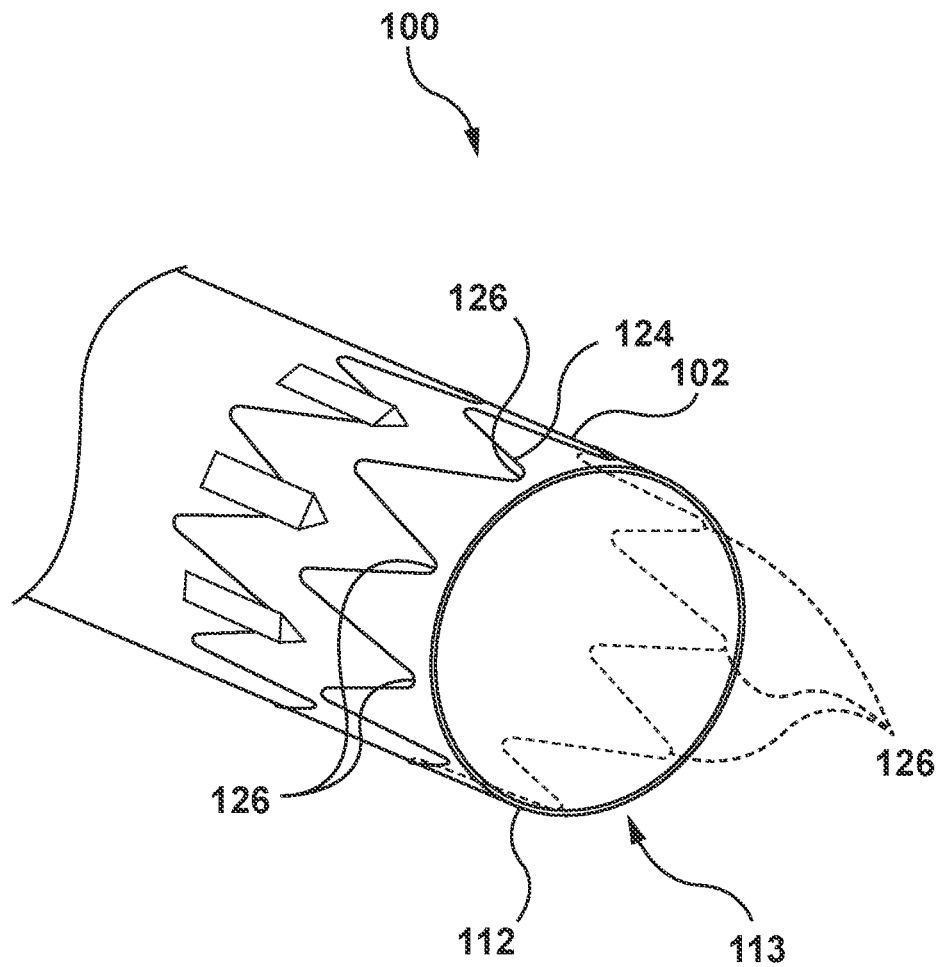
FIG. 3 depicts a perspective view of a second end of the stent-graft prosthesis of FIG. 1, wherein the stent-graft prosthesis is in the radially expanded configuration.

As briefly explained above, in the embodiment of FIG. 1, the proximal end 111 of the stent-graft prosthesis 100 has a closed-web configuration in which the endmost crowns 126 of the seal stent 122 are covered or lined by the graft material 102, as best viewed in FIG. 2. Thus, the endmost crowns 126 of the seal stent 122 do not extend past or beyond the first end 110 of the graft material 102. As utilized herein, "endmost" crowns are the crowns, peaks, or apexes of a stent that are most proximate to an end or edge of the graft material 102 in the direction of the end or edge, such as the first end 110. As best viewed in FIG. 3, the stent-graft prosthesis 100 further includes a closed-web configuration at the distal end 113, with the endmost crowns 126 of the body stent 124F also covered or lined by the material graft 102, i.e., they do not extend outside of or beyond the second end 112 of the graft material 102. In other embodiments hereof (not shown), the endmost crowns of the seal stent 122 and/or the body stent 124F may extend beyond the first end 110 and the second end 112, respectively, of the graft 102 in an open-web configuration.

The plurality of channels 106 are configured to permit blood flow from an upstream side of the stent-graft prosthesis 100 to a downstream side of the stent-graft prosthesis 100 when the stent-graft prosthesis 100 is in the partially expanded configuration. Accordingly, when the stent-graft 100 is in the partially expanded configuration, the channels 106 are configured to relieve pressure associated with pulsatile blood flow on the stent-graft prosthesis 100 during implantation within a body vessel. The partially expanded configuration, as used herein, means that a portion or portions of the stent-graft prosthesis 100 are in a radially compressed state, portions of the stent-graft prosthesis are in a partially expanded state, and at least a portion of the stent-graft prosthesis is in a radially expanded state, as will be described below.

Figure 4:
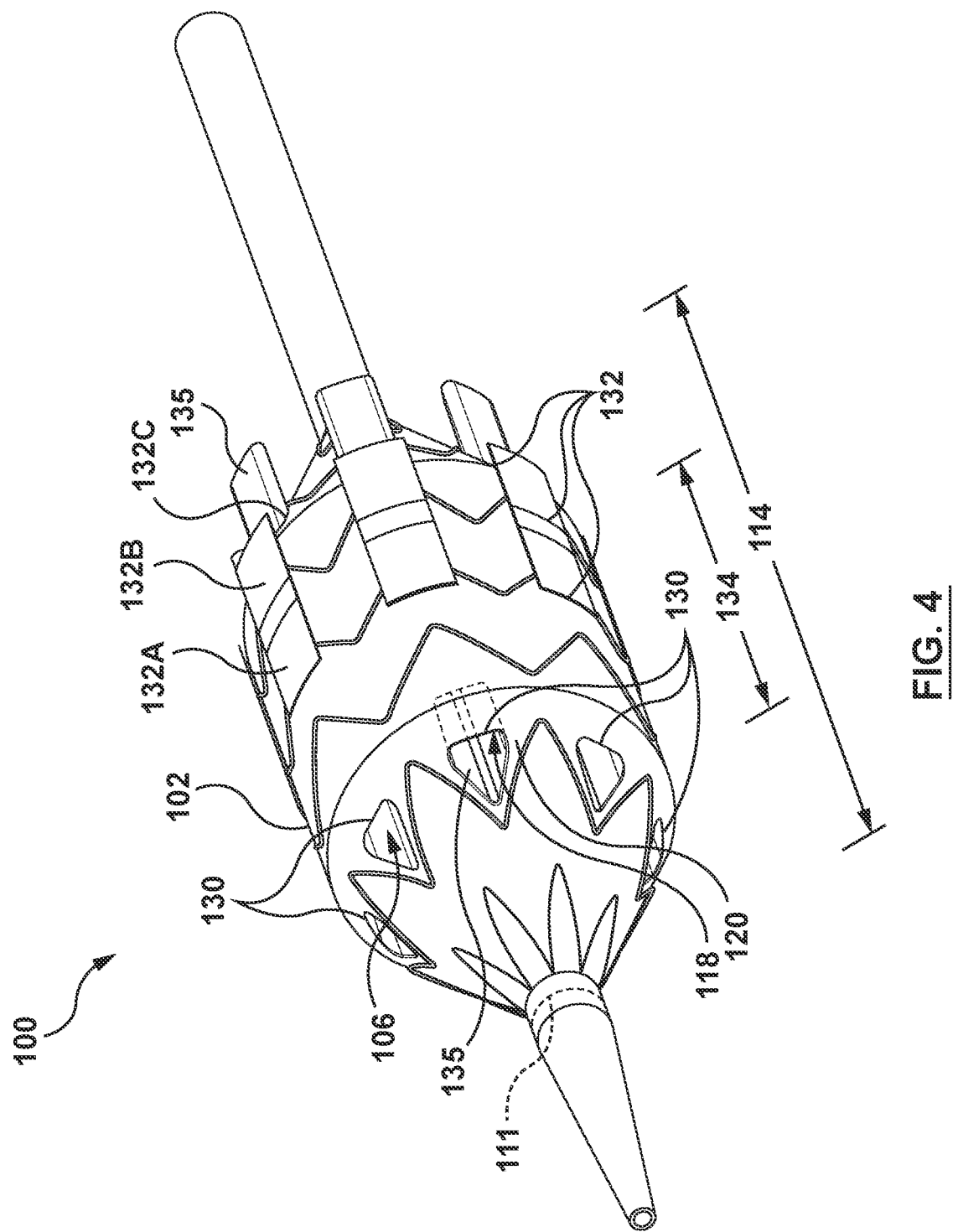
FIG. 4 depicts a perspective view of the stent-graft prosthesis of FIG. 1, wherein the stent-graft prosthesis is in a partially expanded configuration.
Figure 5:
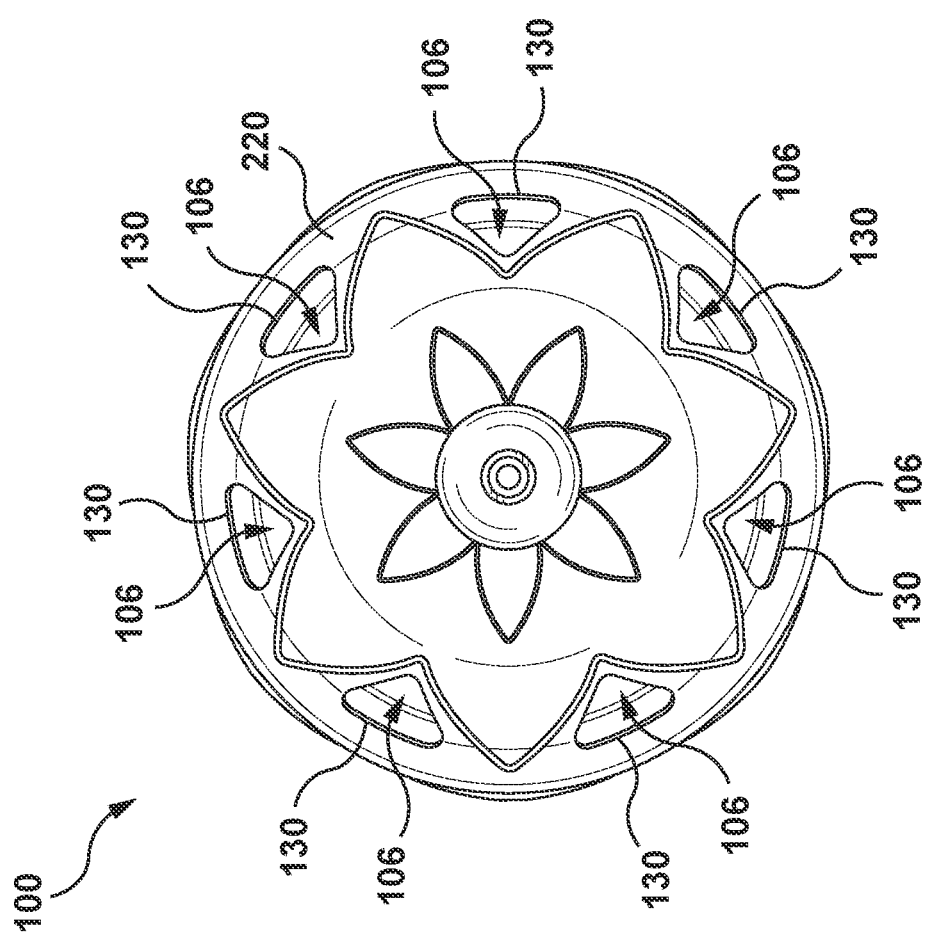
FIG. 5 depicts a view of the stent-graft prosthesis of FIG. 1 from the first end, showing a plurality of channel entrances.
Figure 6:
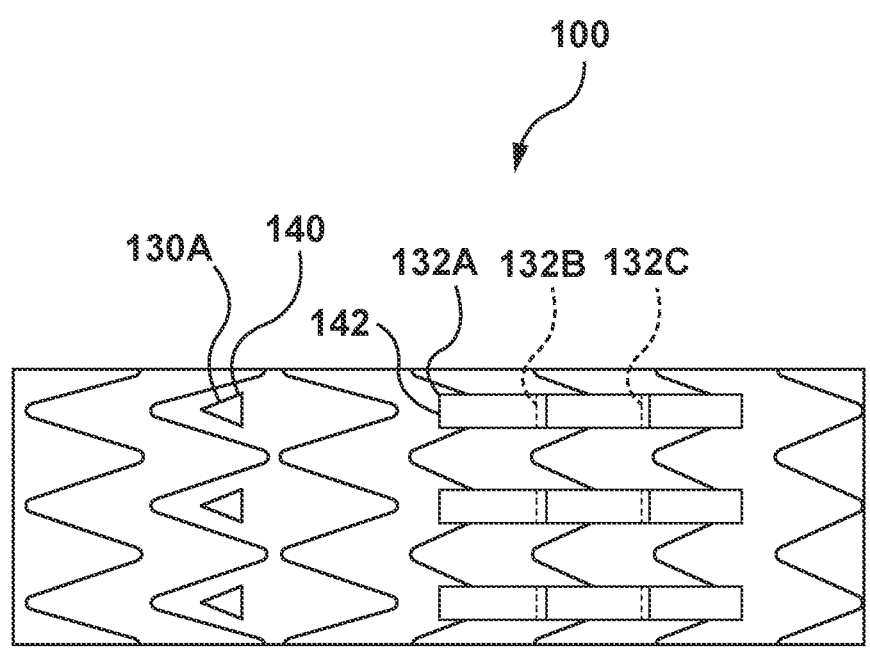
FIG. 6 depicts a side view of the stent-graft prosthesis of FIG. 1, wherein the stent-graft prosthesis is in the radially expanded configuration and a plurality of channel exits is shown.

As best shown in FIGS. 4-6, there are seven (7) channels 106 including seven (7) channel entrances 130 (hereafter referred to as "channel entrances" 130), twenty-one (21) channel exits 132 (hereafter referred to as "channel exits" 132) and a channel lumen 134. The channel lumen 134 extends within and is a portion of the graft lumen 114, extending from the channel entrances 130 to the channel exits 132. The channel lumen 134 may also be thought of as seven (7) channel lumens 134 as the channel entrances 130 are aligned with the channel exits 132, as explained in more detail below.

In the embodiment of FIGS. 1-12, the channel entrances 130 are disposed through the graft material 102 and in fluid communication with the channel lumen 134. Each channel entrance 130 is an opening or aperture extending from the outer surface 120 through the inner surface 118 (not visible in FIG. 4) of the graft material 102. When the stent-graft prosthesis 100 is in the partially expanded configuration, the channel entrances 130 are configured to permit blood flow from outside the graft-material 102 to the channel lumen 134. Each channel exit 132 is disposed through the graft material 102 and in fluid communication with the channel lumen 134. Each channel exit 132 is an opening or aperture extending from the inner surface 118 (not visible in FIG. 4) through the outer surface 120 of the graft material 102, and extending to outside the graft material 102. The channel exits 132 are configured to permit blood flow from the channel lumen 134 to outside the graft material 102 when the stent-graft prosthesis 100 is in the partially expanded configuration. Thus, when the stent-graft prosthesis 100 is in the partially expanded configuration, the channels 106 permit blood flow from an upstream side of the stent-graft prosthesis 100, through the channel lumen 134, to a downstream side of the stent-graft prosthesis 100. While the stent-graft prosthesis 100 is shown with seven (7) channels 106 including seven (7) channel entrances 130 and twenty-one (21) channel exits 132, this is by way of example and not limitation, and there may be more or fewer channels 106, channel entrances 130 and channel exits 132. The shape of the channel entrances 130 may be different than the shape of the channel exits 132 to facilitate the difference in the natural taper of the stent-graft prosthesis 100 in the partially expanded configuration, as described below.

In the embodiment of FIGS. 1-12, each channel entrance 130 includes three (3) corresponding channel exits 132 that are circumferentially aligned with and longitudinally spaced from the corresponding channel entrance 130. As best shown in FIG. 6, each of the channel exits 132A, 132B, and 132C is longitudinally or axially spaced from the corresponding channel entrance 130A by a different length or amount. In other words, the channel exit 132A is located closer to the channel entrance 130A than the channel exit 132B is to the channel entrance 130A, and the channel exit 132B is located closer to the channel entrance 130A than the channel exit 132C is to the channel entrance 130A. While each channel entrance 130 is shown with three (3) corresponding channel exits 132, this is by way of example and not limitation, and each channel entrance 130 may have more or fewer corresponding channel exits 132. The reason for having more than one channel exit 132 per channel entrance 130 and for the channel exits 132 to be longitudinally spaced is for at least one of the channel exits to 132 to be open at different stages of deployment of the stent-graft prosthesis 100, as will be explained in more detail below. Further, FIG. 6 shows that the valve assembly/flap (described in more detail below) of channel exit 132A overlaps with channel exit 132B (hence channel exit 132B is shown dashed). Similarly, the valve assembly/flap of channel exit 132B overlaps with channel exit 132C. This overlap is better seen in FIGS. 10, for example. However, this is not meant to be limiting and the flaps need not overlap. Moreover, while the corresponding channel entrance 130 and channel exits 132 are described as circumferentially aligned, this is not meant to be limiting, and the corresponding channel entrance 130 and channel exits 132 need not be circumferentially aligned.

Figure 7:
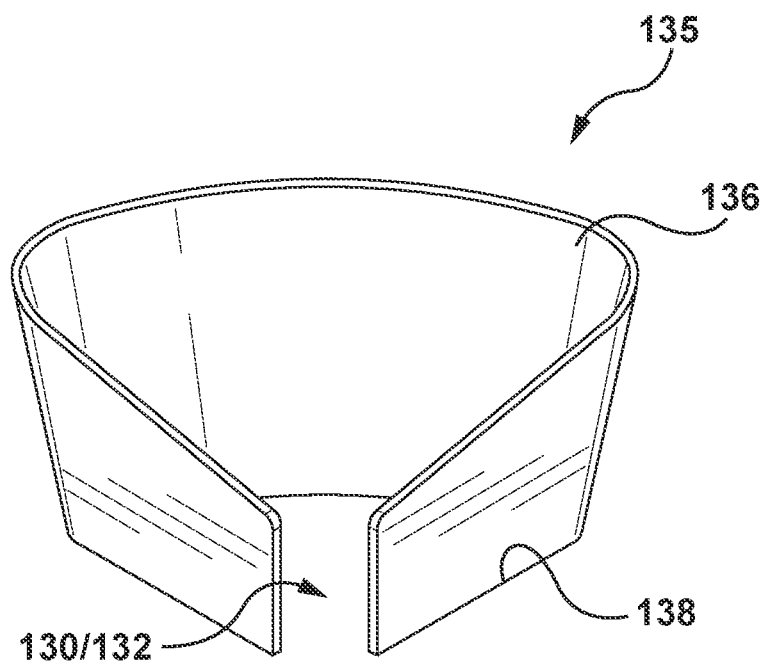
FIG. 7 depicts a perspective view of a valve assembly of the channel entrance or the channel of the stent-graft prosthesis of FIG. 1, wherein the valve assembly is in an open state.
Figure 8:
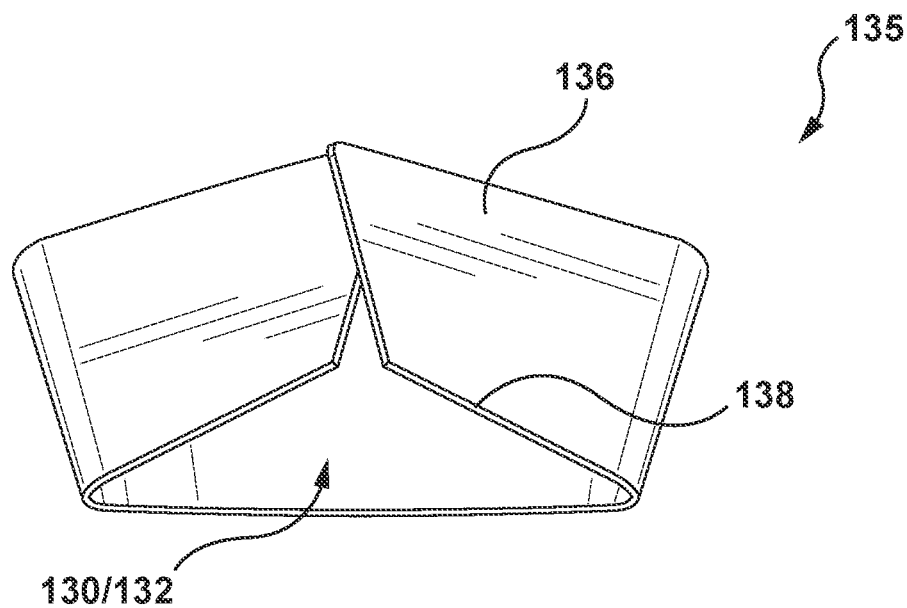
FIG. 8 depicts a perspective view of the valve assembly of FIG. 7, wherein the valve assembly is in a closed state.

In an embodiment, each of the channel entrances 130 and/or each of the channel exits 132 may include a valve assembly 135, coupled thereto, as shown in FIGS. 7 and 8. Each valve assembly 135 includes an open state and a closed state. When the valve assembly 135 is in the open state, the valve assembly 135 is configured to permit blood flow there through. The open state of each valve assembly 135 corresponds to the partially expanded state of the adjacent body stent 124 of the channel entrance 130 or the channel exit 132 to which the valve assembly 135 is coupled, as will be described below. When the valve assembly 135 is in the closed state, the valve assembly 135 is configured to prevent blood flow there through. The closed state of each valve assembly 135 corresponds to the radially collapsed and the radially expanded configurations of the adjacent body stent 124 of the channel entrance 130 or the channel exit 132 to which the valve assembly 135 is coupled, as will also be described below. Each valve assembly 135 may be coupled to the corresponding channel entrance 130 or channel exit 132 by methods such as, but not limited to adhesives, sewing, fusing, or any other suitable method.

In an embodiment, each valve assembly 135 is a flap valve assembly 135. Each flap valve assembly 135 has a generally triangular shape when in the open state, as shown in FIG. 7, and a generally flat, rectangular shape when in the closed state, as shown in FIG. 8. As best viewed in FIG. 7, each flap valve assembly 135 includes a collar 136. A first edge 138 of the collar 136 is coupled to a first edge 140 (see FIG. 6) of the channel entrance 130 or a first edge 142 (see FIG. 6) of the channel exit 132. When coupled to the channel entrance 130 or the channel exit 132, the flap valve assembly 135 changes shape as the portion of the stent graft prosthesis 100 adjacent the channel exit 130 or the channel exit 132 transitions from the radially compressed state, to the partially expanded state, and then to the radially expanded state. Thus, as explained in more detail below, when the portion of the stent-graft prosthesis 100 adjacent a channel entrance 130 or a channel exit 132 to which the flap valve assembly 135 is coupled is in the radially compressed configuration for delivery, the flap valve assembly 135 is closed. When the portion of the stent-graft prosthesis 100 adjacent a channel entrance 130 or a channel exit 132 to which the flap valve assembly 135 is coupled radially expands from the radially compressed state to the partially expanded state, the flap valve assembly transitions to the open state. When the portion of the stent-graft prosthesis 100 adjacent a channel entrance 130 or a channel exit 132 to which the flap valve assembly 135 is coupled expands to the radially expanded configuration, the flap valve assembly 135 correspondingly transitions to the closed state, preventing blood flow through the corresponding channel entrance 130 or channel exit 132.

In an embodiment, each valve assembly 135 extends longitudinally, generally parallel to the central longitudinal axis LA of the graft material 102, as best shown in FIG. 4. Thus, each valve assembly 135 at each channel entrance 130 extends from the channel entrance 130 distally inside of the graft material 102 (i.e., within the graft-lumen 114). Further, each valve assembly 135 at each channel exit 132 extends from the channel exit 132 outside the graft material 102 of the stent-graft prosthesis 100.

While described herein with a valve assembly 135 at each channel entrance 130 and each channel exit 132, this is not meant to be limiting, and in other embodiments, each channel entrance 130 and each channel exit 132 may or may not have a valve assembly 135. Moreover, while each valve assembly 135 has been described as a flap valve assembly 135, this is by way of example and not limitation, and each valve assembly 135 may have a valve design other than a flap valve. Further, each valve assembly 135 may be of a similar or different valve design in any combination.

The operation of the stent-graft prosthesis 100 will now be explained with reference to FIGS. 9-12, which are sectional cutaway views of a vessel illustrating the delivery, positioning and deployment of the stent-graft prosthesis 100 at the site of a vessel abnormality, which in FIGS. 9-12 is an aneurysm. However, this is by way of example and not limitation and embodiments of the stent-graft prosthesis 100 may be utilized with other vessel abnormalities including, but not limited to dissections and transections.

Figure 9:
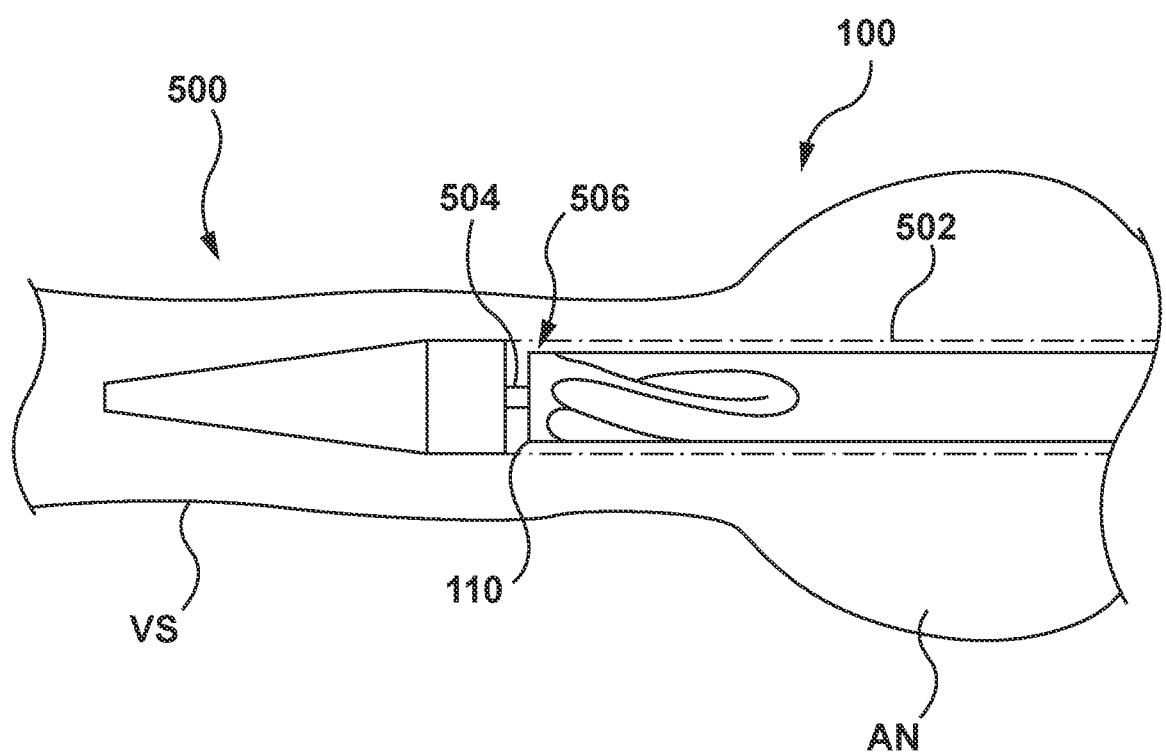
FIG. 9 depicts a side view of the stent-graft prosthesis of FIG. 1 in situ, wherein the stent-graft prosthesis is disposed on a distal portion of a delivery system in a radially compressed configuration.

Referring now to FIG. 9, the stent-graft prosthesis 100 is disposed on a distal portion of a delivery system 500 in the radially compressed configuration. The delivery system 500 includes at least an outer sheath 502 and an inner shaft 504 having a tip capture mechanism 506 mounted thereon. The proximal end 111 of the stent-graft prosthesis 100 is releasably coupled to the tip capture mechanism 506. The stent-graft prosthesis 100 is mounted on the inner shaft 504 and the outer sheath 502 encapsulates, covers, or restrains the stent-graft prosthesis 100 in the radially compressed configuration for delivery thereof. The delivery system 500 is advanced to a desired treatment location of an aneurysm AN in a vessel VS. In embodiments hereof, the delivery system 500 may be similar to the Captiva Delivery System, manufactured by Medtronic Vascular, Inc. of Santa Rosa, California, or a delivery system as described in U.S. Patent Application Publication No. 2009/0276027 to Glynn, or U.S. Pat. No. 8,882,828 to Kinkade et al., each of which is incorporated by reference herein in its entirety.

Figure 10:
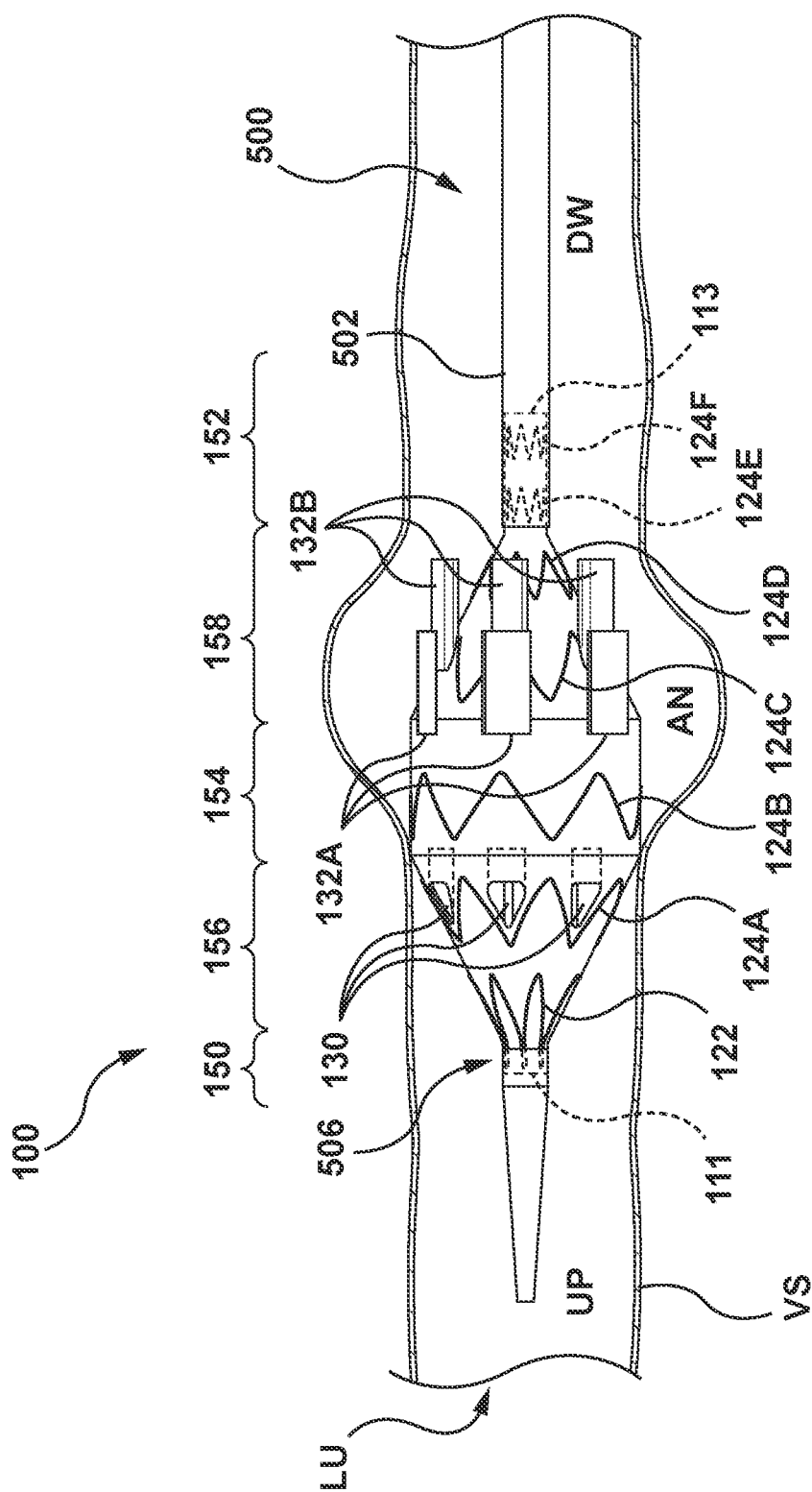
FIG. 10 depicts a side view of the stent-graft prosthesis of FIG. 1 in situ, wherein the stent-graft prosthesis is disposed on a distal portion of a delivery system and is in the partially expanded configuration.

Once the stent-graft prosthesis 100 is at the desired treatment location within the vessel VS, the stent-graft prosthesis 100 may be deployed from the delivery system 500. The outer sheath 502 of the delivery system 500 is retracted to release a portion the stent-graft prosthesis 100. The released portion of the stent-graft prosthesis 100 radially expands within the vessel VS and the stent-graft prosthesis 100 transitions to a partially expanded configuration. When in the partially expanded configuration shown in FIG. 10, a first or tip-capture portion 150 of the stent-graft prosthesis 100, including at least the proximal end 111, is restrained in the radially compressed state by the tip capture mechanism 506. A second or distal constrained portion 152 including at least the distal end 113 is restrained in the radially compressed state by the outer sheath 502. At the deployment moment shown in FIG. 10, the distal restrained portion 152 further includes the body stents 124E and 124F. A third or expanded portion 154 of the stent-graft prosthesis 100 expands to the radially expanded state to conformingly engage the inner wall of the vessel VS. In FIG. 10, the expanded portion 154 includes the body stent 124B. A fourth or tapered inlet portion 156 is disposed between the tip-capture portion 150 and the expanded portion 154 and is held in the partially expanded state by the tip-capture portion 150 in the radially compressed configuration and the expanded portion 154 in the radially expanded configuration. The tapered inlet portion 156 includes the seal stent 122, the body stent 124A, and the channel entrances 130. A fifth or tapered outlet portion 158 is disposed between the expanded portion 154 and the distal constrained portion 152 and is held in the partially expanded state by the expanded portion 154 in the radially expanded configuration and the distal constrained portion 152 in the radially compressed configuration. The tapered outlet portion 158 includes the body stents 124C and 124D, and the channel exits 132A and 132B, respectively.

When in the partially expanded configuration of FIG. 10, the stent-graft prosthesis 100 generally occludes the lumen LU of the vessel VS. Thus, as can be seen in FIG. 10, absent the channel entrances 130, blood pressure against the stent-graft prosthesis may cause the stent-graft prosthesis 100 to move during deployment. Also, blood flow past the stent-graft prosthesis 100 is blocked, thereby depriving blood flow to vessels downstream of the stent-graft prosthesis 100. However, when in the partially expanded configuration of FIG. 10, blood flow is enabled through the channels 106. In particular, as explained above, the channel entrances 130 are disposed in the tapered inlet portion 156 of the partially deployed stent-graft prosthesis 100, distal of the first end 110 of the graft material 102. In this partially expanded state of the tapered inlet portion 156, the channel entrances 130 and the associated valve assemblies 135 are open, thus enabling blood flow into the channel lumen 134 (i.e., the graft lumen 114). Similarly, the tapered outlet portion 158 is in the partially expanded state. Therefore, the channel exits 132A, 132B disposed at the tapered outlet portion 158, and their associated valve assemblies 135, are open, thereby enabling blood flow out of the channel lumen 134 through the channel exits 132A, 132B. Thus, blood from an upstream side UP of the stent-graft prosthesis 100 is permitted to travel through the channels 106 to the downstream side DW of the stent-graft prosthesis 100. More precisely, blood on the upstream side UP of the stent-graft prosthesis 100 enters through the channel entrances 130, travels through the channel lumen 134, and exits to the downstream side DW of the stent-graft prosthesis 100 through the channel exits 132A and 132B. The flow of blood through the channels 106 from the upstream side UP to the downstream side DW of the stent-graft prosthesis 100 relieves pressure associated with pulsatile blood flow on the upstream side UP of the stent-graft prosthesis 100, and more specifically on the outer surface 120 of the graft material 102 of the tapered inlet portion 156 of the stent-graft prosthesis 100. The flow of blood through the channels 106 from the upstream side UP to the downstream side DW of the stent-graft prosthesis 100 also provides blood supply to vessels downstream of the stent-graft prosthesis 100. When the pressure associated with the pulsatile blood flow is relieved on the upstream side UP by the channels 106 during deployment of the stent-graft prosthesis 100, the stent-graft prosthesis 100 can be more precisely positioned. In addition, the position of the stent-graft prosthesis 100 can be more easily maintained during deployment of the stent-graft prosthesis 100.

Figure 11:
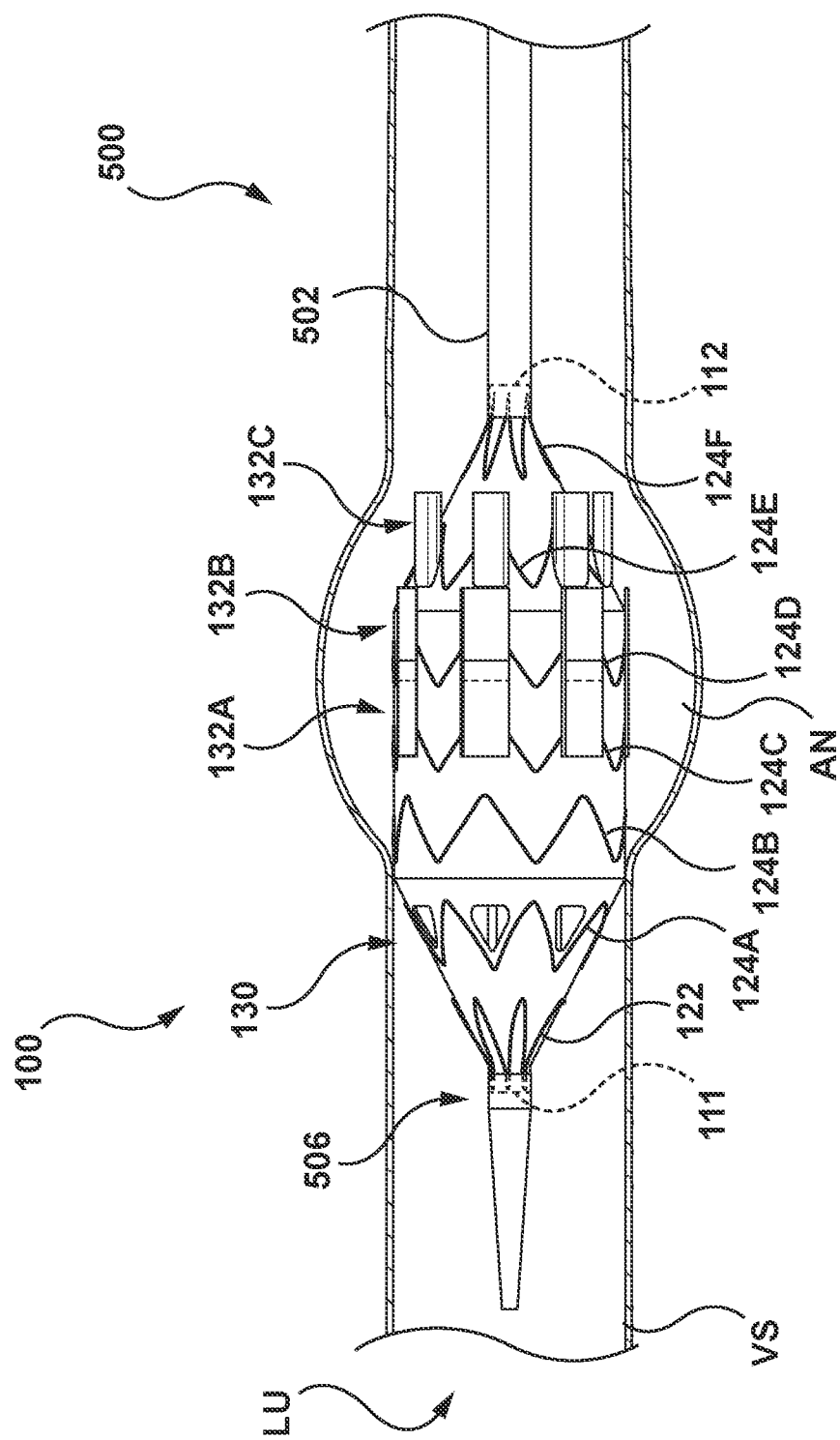
FIG. 11 depicts another side view of the stent-graft prosthesis of FIG. 1 in situ, wherein the stent-graft prosthesis is in the partially expanded configuration.

The blood flow explained above is at the stage of deployment shown in FIG. 10. As the outer sheath 502 continues to be retracted to release the stent-graft prosthesis 100, the blood flow from the upstream side UP to the downstream side DW of the stent-graft prosthesis 100 through the channels 106 is maintained. In particular, as each successive body stent 124 is released from the outer sheath 502 during deployment of the stent-graft prosthesis 100, each released body stent 124 expands first to a partially expanded state and then to a radially expanded state. More specifically, as each body stent 124 expands to the partially expanded state, each body stent 124 transitions from the distal constrained portion 152 of the stent-graft prosthesis 100 to the tapered outlet portion 158 of the stent-graft prosthesis 100. In the example of FIG. 10, the next body stent 124 to be released would be the body stent 124E. When the body stent 124E is released and permitted to expand to the partially expanded state, the body stent 124 of the tapered outlet portion 158 closest to the first end 111, in the example of FIG. 10, the body stent 124C, is concurrently permitted to expand to the radially expanded state and transitions to the expanded portion 154, as shown in FIG. 11. As body stent 124C radially expands to the radially expanded state, the channel exits 132A and their associated valve assemblies 135 are closed due to the expansion. At the stage shown in FIG. 11, body stent 124D has also radially expanded to the radially expanded state, thereby closing channels exits 132B and their associated valve assemblies 135. Further, when the body stent 124E expands to the partially expanded state upon release from the outer sheath 502, the corresponding valve assemblies 135 of the adjacent channel exits 132C transition from the closed state to the open state to permit blood to exit the channels 106 therethrough, as shown in FIG. 11. Thus, blood flow through the channels 106 is maintained during the deployment of the stent-graft prosthesis 100, with blood entering the channel entrances 130, traveling through the channel lumen 134, and exiting one or more of the channel exits 132A, 132B, and 132C as the stent-graft prosthesis 100 is deployed.

Figure 11A:
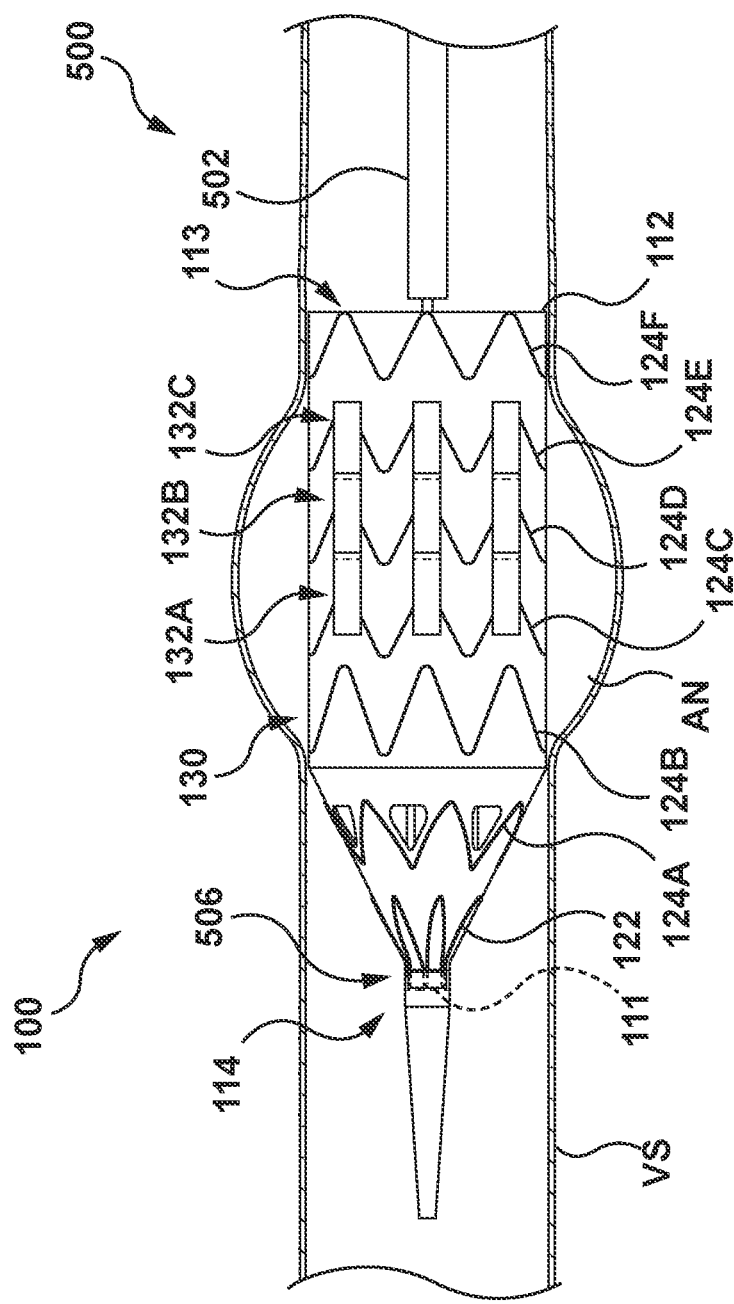
FIG. 11A depicts a side view of the stent-graft prosthesis of FIG. 1 in situ, wherein the stent-graft prosthesis is in a partially expanded configuration with the proximal or upstream end radially compressed and the distal or downstream end radially expanded.
Figure 12:
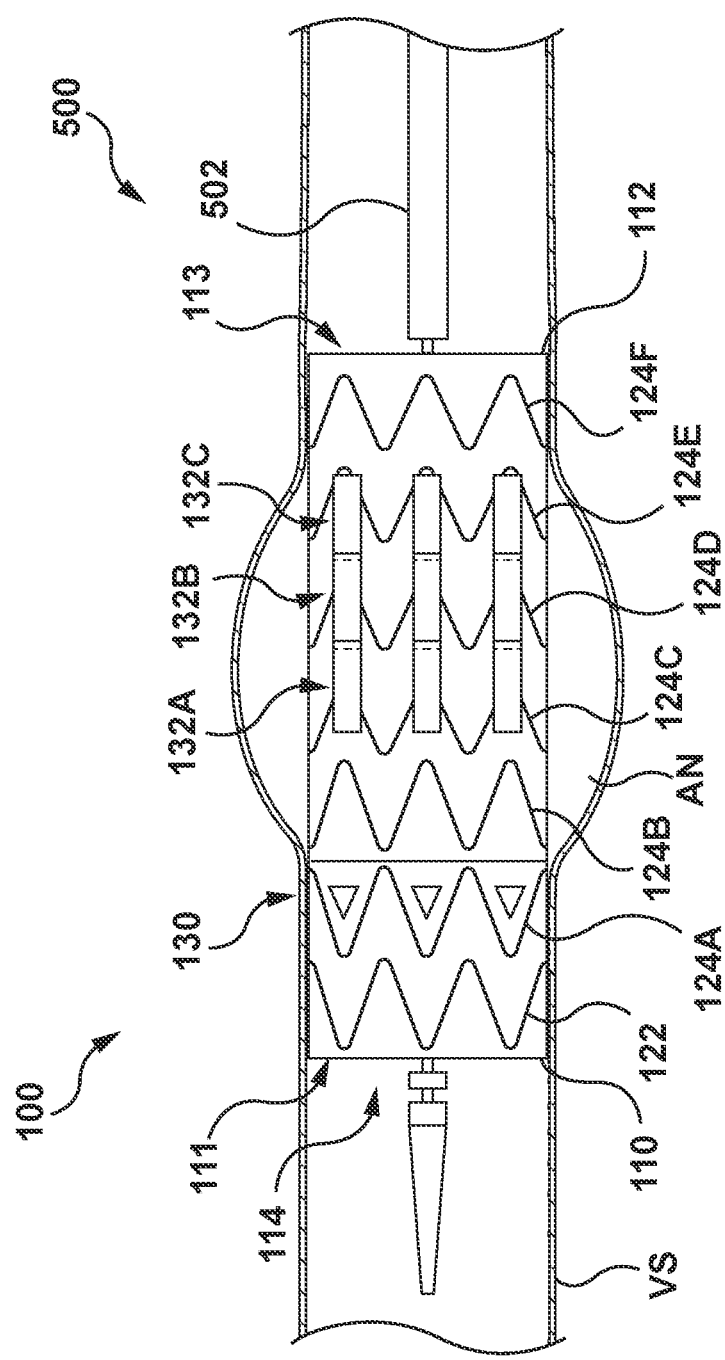
FIG. 12 depicts a side view of the stent-graft prosthesis of FIG. 1 in situ, wherein the stent-graft prosthesis is in the radially expanded configuration and the valve assemblies are in the closed state.

When final deployment of the stent-graft prosthesis 100 is desired, the outer sheath 502 is retracted to release the second end 113 of the stent-graft prosthesis 100, as shown in FIG. 11A. In this configuration, the channel exits 132A, 132B, 132C are all closed, but the channel entrances 130 are open because first end 111 of the stent-graft prosthesis 100 is captured by the tip capture mechanism 506. Blood flows into the channel entrances 130, into the graft lumen 114, and exits through the second end 113 of the stent-graft prosthesis 100 distal of the aneurysm AN. The tip capture mechanism 506 is then actuated to release the first end 111 of the stent-graft prosthesis 100 to transition the stent-graft prosthesis 100 to the radially expanded configuration within the vessel VS, as shown in FIG. 12. When in the radially expanded configuration, each of the channel entrances 130 and each of the channel exits 132 are in the closed state and blood is permitted to flow through the graft lumen 114 from the proximal end 111 to the distal end 113 of the stent-graft prosthesis 100, thereby isolating the aneurysm AN from blood normal pressure and reducing the chance of vessel rupture.

Figure 11B:
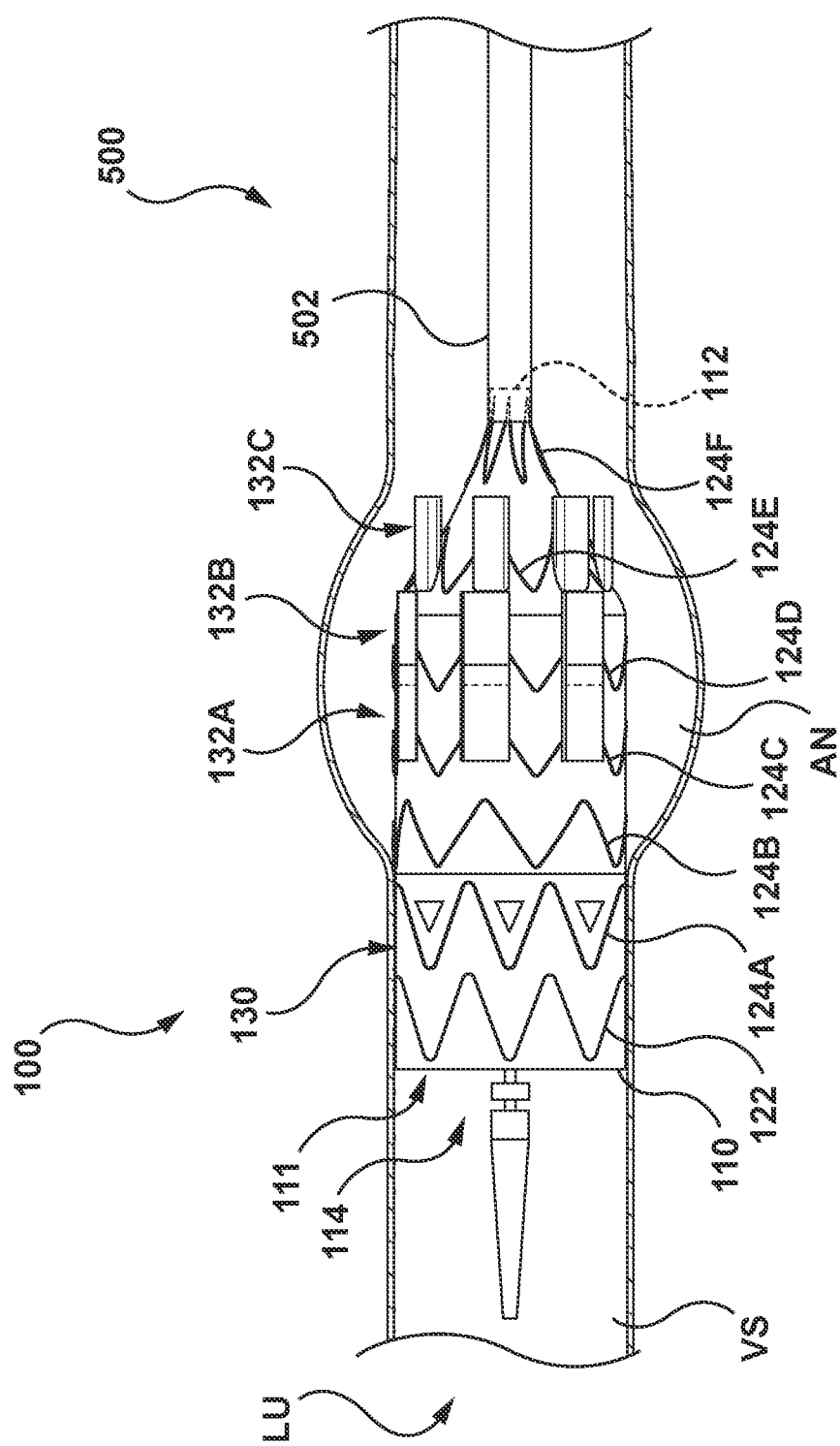
FIG. 11B depicts a side view of the stent-graft prosthesis of FIG. 1 in situ, wherein the stent-graft prosthesis is in a partially expanded configuration with the proximal or upstream end radially expanded and the distal or downstream end radially compressed.

FIG. 11B shows an embodiment wherein the first end 111 of the stent-graft prosthesis 100 is in the radially expanded configuration (tip capture mechanism 506 has been actuated) and the second end 113 of the stent-graft prosthesis 100 is still captured in the sheath 502. This can occur between the step shown in FIG. 11 and the full release of the stent-graft prosthesis 100 as shown in FIG. 12. Thus, instead of releasing the second end 113 first, as shown in FIG. 11A, the first end 111 is released first. However, in other embodiments, the first end 111 of the stent-graft prosthesis 100 may be radially expanded prior to any other portion of the stent-graft prosthesis 100 in order to allow radial expansion of the seal stent 122 to secure the stent-graft. In either situation, with the first end 111 in the radially expanded configuration, blood enters the graft lumen 114. In a conventional stent-graft, with the second, downstream end still captured in delivery system, the blood is trapped within the graft lumen. With the stent-graft prosthesis 100 disclosed herein, however, blood may exit the graft lumen 114 through the channel exits 132. If the stent-graft prosthesis 100 is to be used in a method wherein the first end 111 is radially expanded prior to the remainder of the stent-graft prosthesis 100, as described, then the channel entrances 130 are not needed.

FIGS. 13-19 illustrate a stent-graft prosthesis 200 in accordance with another embodiment hereof. In the embodiment shown, the stent-graft prosthesis 200 includes a graft material 202, a frame 204, and a plurality of channels 206 (not shown in FIG. 13—see FIG. 15-16). The stent-graft prosthesis 200 has a radially compressed configuration for delivery, a radially expanded configuration when deployed, and a partially expanded configuration when transitioning between the radially compressed and the radially expanded configurations. The stent-graft prosthesis 200 is of a closed-web configuration. However, the stent graft prosthesis 200 may instead be an open web configuration.

Figure 13:
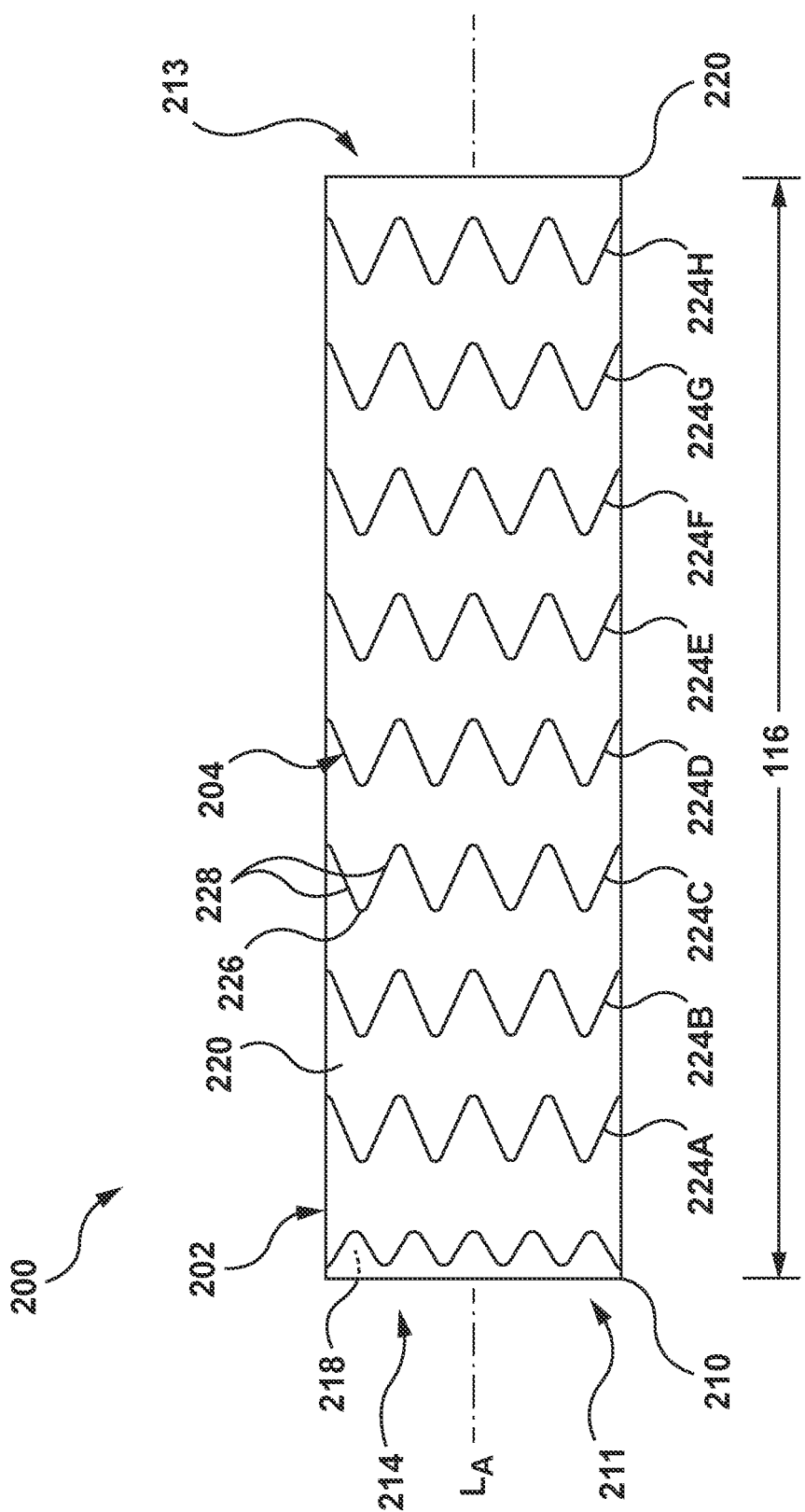
FIG. 13 depicts a side view of a stent-graft prosthesis having at least one channel for relieving pulsatile blood pressure according to another embodiment hereof, wherein the stent-graft prosthesis is in a radially expanded configuration.

The graft material 202 is of a generally tubular shape having a central longitudinal axis $L_A$, a first end or edge 210, a second end or edge 212, and a graft lumen 214 extending from the first end 210 to the second end 212, as shown in FIG. 13. The graft material 202 has a longitudinal length 216, which may vary based upon the application. The graft material 202 further includes an inner surface 218 and the outer surface 220. In an embodiment, the first end 210 of the graft material 202 may be referred to as a proximal or an upstream end or edge 210 of the graft material 202. In the embodiment shown, the first end 210 of the graft material is also a first, proximal or upstream end or edge 211 of the stent-graft prosthesis 200. The second end 212 of the graft material 202 may be referred to as a distal or a downstream end or edge 212 of the graft material 202. In the embodiment shown, the second end 212 of the graft material 202 is also a second, distal or downstream end or edge 213 of the stent-graft prosthesis 200. For a stent-graft prosthesis for an abdominal aortic aneurysm delivered from the femoral artery, the proximal or upstream end 211 of the stent-graft prosthesis 200 is the end that is coupled to a tip capture mechanism of a delivery system. The graft material 202 may be formed from any suitable graft material as previously described with respect to the graft material 102.

As shown in FIG. 13, the frame 204 includes a sealing or seal stent 222 and a plurality of body stents 224. The frame 204 is configured to support the graft material 202. In the embodiment illustrated in FIG. 13, the stent-graft prosthesis 200 is shown in the radially expanded configuration and includes one (1) seal stent 222 adjacent to the first end 210, and eight (8) body stents 224 axially spaced between the first end 210 and the second end 212 of the graft material 102. Although shown with eight (8) body stents 224A, 224B, 224C, 224D, 224E, 224F, 224G, and 224H, it will be understood that the stent-graft prosthesis 200 may include more or fewer of body stents 224 depending upon the desired length 216 of the stent-graft prosthesis 200 and/or the intended application. The seal stent 222 and each of the body stents 224 are self-expanding and each includes a radially compressed state for delivery, a radially expanded state when deployed, and a partially expanded state when transitioning between the radially compressed state and the radially expanded state. The seal stent 222 and each of the body stents 224 may be a sinusoidal patterned ring including a plurality of crowns or bends 226 and a plurality of struts or straight segments 228 with each crown 226 being formed between a pair of adjacent struts 228. While shown with a particular pattern, the seal stent 222 and the body stents 224 may have different patterns and configurations. As described in more detail below, the body stents 224 are disposed on the outer surface 220 of the graft material 202.

The seal stent 222 is coupled to the graft material 202. When the stent-graft prosthesis 200 is in the radially expanded configuration, the seal stent 222 is configured with sufficient radial spring force to conformingly and sealingly engage a wall of a vessel to prevent blood flow between the wall of the vessel and the outer surface 220 of the graft material 202. The seal stent 222 may be coupled to the graft material 202 by stitches, sutures, or any other suitable method. In the embodiment shown in FIG. 13, the seal stent 222 is coupled to the outer surface 220 of the graft material 102. However, in alternate embodiments, the seal stent 222 may be coupled to the inner surface 218 of the graft material 202.

Figure 14:
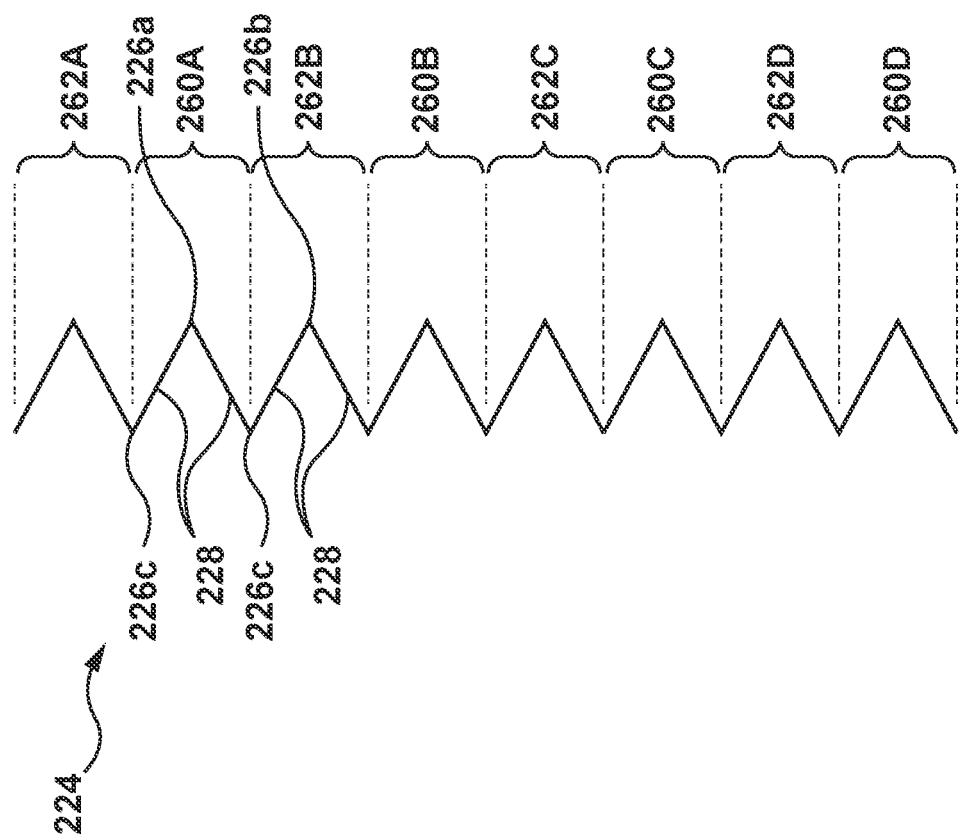
FIG. 14 depicts a side view of a body stent of the stent-graft prosthesis of FIG. 13, wherein the body stent has been cut and laid flat for illustrative purposes.

In the embodiment illustrated in FIG. 14, which is a body stent 224 cut and flattened for illustrative purposes, each body stent 224 includes four (4) first segments 260. Each first segment 260 is circumferentially separated from an adjacent first segment 260 by a second segment 262. Thus, the body stent 224 includes four (4) second segments 262. Each first segment 260 includes one (1) crown 226a and two (2) adjacent struts 228. Each second segment 262 includes one (1) crown 226b and two adjacent struts 228. Further, there is a crown 226c where each first segment 260 meets an adjacent second segment 262. While each body stent 224 is described as having four (4) first segments 260 and four (4) second segments 262, this is by way of example and not limitation, and each body stent 224 may have more or fewer of first and second segments 260, 262. Additionally, while each first segment 260 and second segment 262 is described with one (1) crown 226 and two (2) adjacent struts 228, this, too, is by way of example and not limitation, and each first segment 260 and/or each second segment 262 may have more crowns 226 and adjacent struts 228. Even further, while the crown 226a of each first segment 260 is facing a specific direction, and the crown 226b of each second segment 262 is facing in the same direction, this is not meant to be limiting, and each crown 226a/226b of each first section 260 and second section 262 may alternatively face the opposite direction in any combination.

Figure 15:
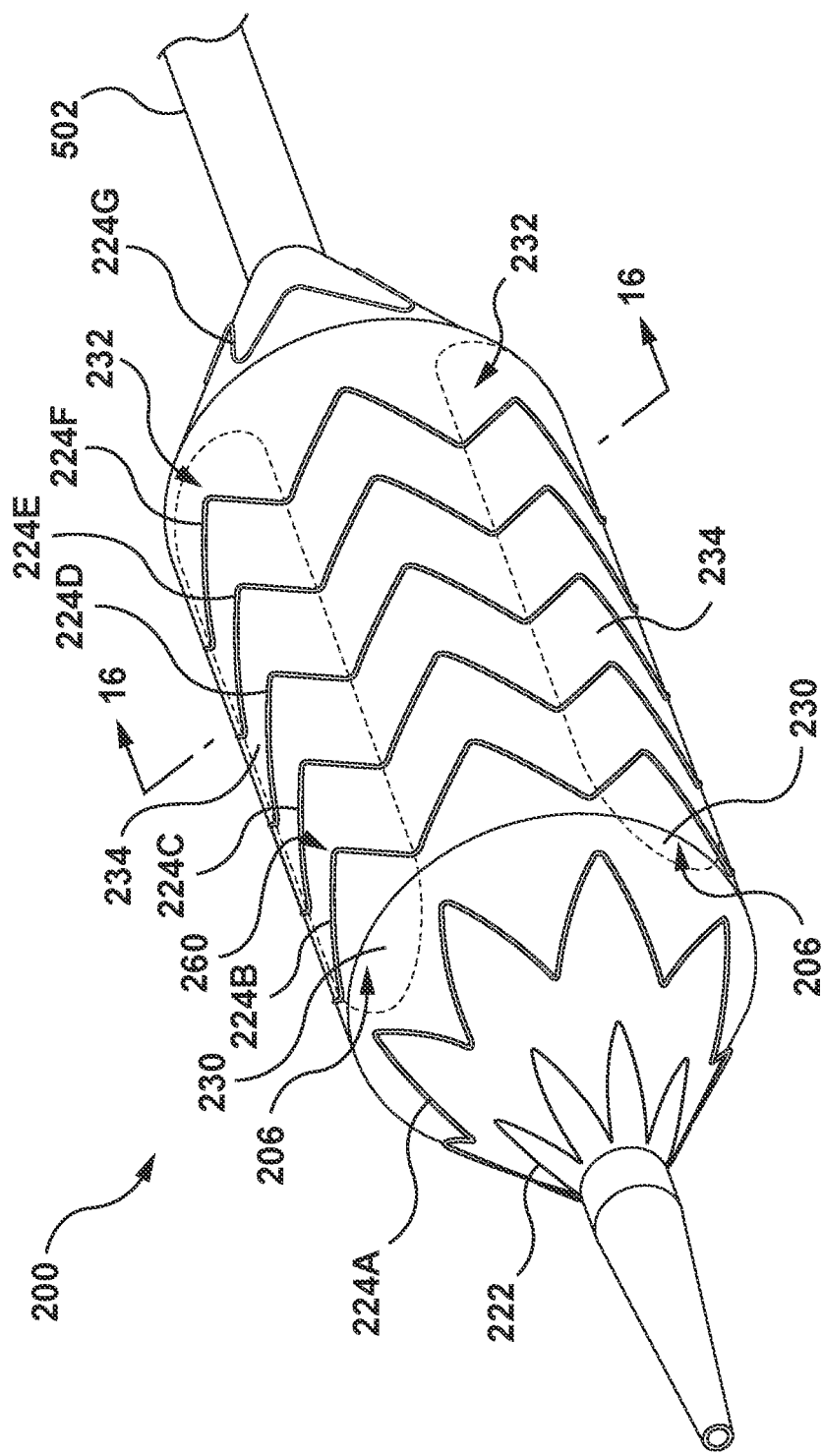
FIG. 15 depicts a perspective view of the stent-graft prosthesis of FIG. 13, wherein the stent-graft prosthesis is in a partially expanded configuration.
Figure 16:
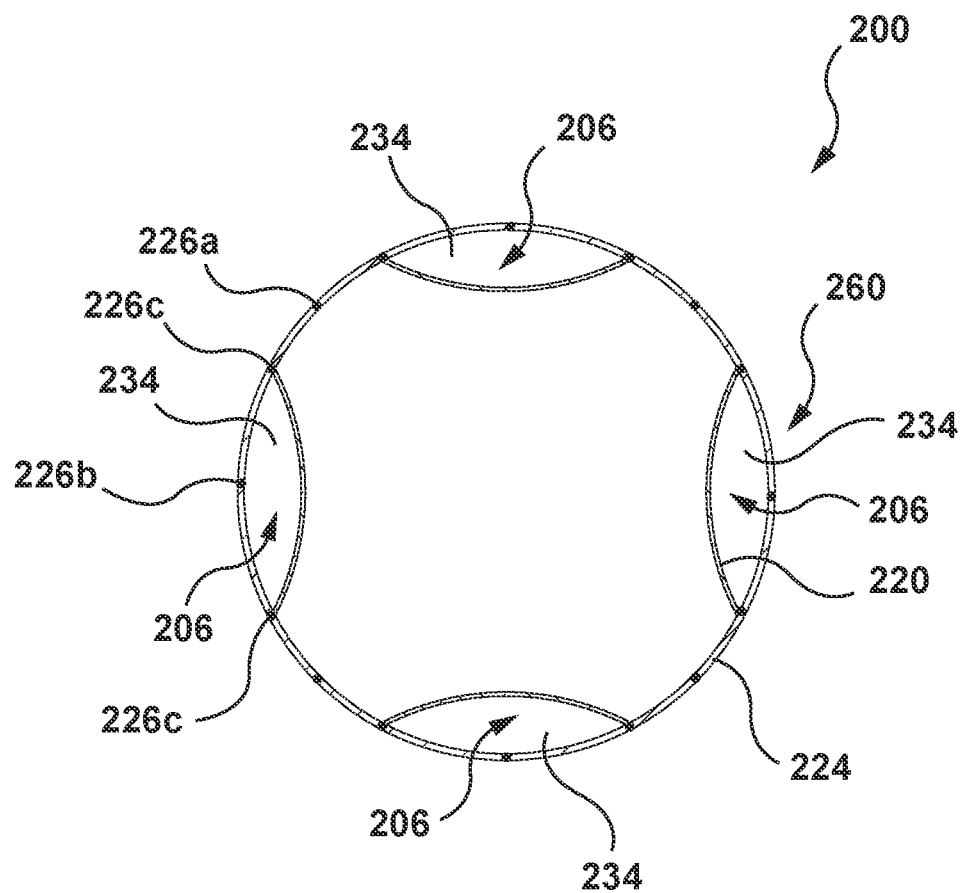
FIG. 16 depicts a cross-sectional view of the stent-graft prosthesis taken along line 16-16 of FIG. 15.

Each second segment 262 is coupled to the outer surface 220 of the graft material 202 by methods such as, but not limited to stitches, sutures, or any other suitable method. Each first segment 260 is not coupled to the graft material 202. As shown in FIGS. 15 and 16, and explained in more detail below, each of the channels 206 is formed between an outer surface 220 of the graft material 202 at the location of one of the first segments 260 and a vessel wall when the stent-graft prosthesis 200 is in a partially expanded configuration.

When each body stent 224 is assembled as part of the frame 204 of the stent-graft prosthesis 200, as best shown in FIG. 15, which is a perspective illustration of the stent-graft prosthesis 200 in the partially expanded configuration, the first segments 260 of each body stent 224 are circumferentially aligned with the first segments 260 of a longitudinally adjacent body stent 224.

Each channel 206 is configured to relieve pressure associated with pulsatile blood flow on the stent-graft prosthesis 200 during implantation within a body vessel. Accordingly, each channel 206 is configured to permit blood flow from an upstream side of the stent-graft prosthesis 200 to a downstream side of the stent-graft prosthesis 200 when the stent-graft prosthesis is in the partially expanded configuration, as shown in FIG. 15. The partially expanded configuration, as used herein, means that a portion or portions of the stent-graft prosthesis 200 is/are in a radially compressed state and at least a portion of the stent-graft prosthesis 200 is in a radially expanded state, as will be described in more detail below. In the embodiment shown in FIG. 15, the first end 211 is the upstream side of the stent-graft prosthesis 200 and the second end 213 is the downstream side of the stent-graft prosthesis 200.

As best shown in FIG. 15, each channel 206 includes a channel lumen 234 extending from a channel entrance 230 distal of the first end 210 of the graft material 202 to a channel exit 232 proximal of the second end 212 of the graft material 202. Each channel entrance 230 is formed at the first body stent 224 distal of the first end 211 that includes first segments 260 that are unattached to the graft material 202. In the embodiment shown in FIG. 15, the first body stent distal of the first end 211 that includes first segments 260 that are unattached to the graft material 202 is the body stent 224B (i.e., the second body stent). However, this is not meant to be limiting and the channel entrances 230 may be formed at other body stents depending on, for example, the locations of the body stents, their spacing, the expanded diameter of the stent-graft prosthesis 200, and other factors that would be recognized by those skilled in the art. The formation of the channel exits 232 will be discussed in more detail below. Each channel entrance 230 is configured to permit blood flow to the corresponding channel lumen 234 and each channel exit 232 is configured to permit blood flow from the corresponding channel lumen 234 when the stent-graft prosthesis 200 is in the partially expanded configuration.

As best shown in FIG. 16, the stent-graft prosthesis 200 includes four (4) channels 206. As noted above, each channel lumen 234 is formed between the outer surface 220 of the graft material 202 and the adjacent wall of the vessel at the locations of the first segments 260 when the stent-graft prosthesis 200 is in the partially expanded configuration. While described with four (4) channels 206, this is by way of example and not limitation, and there may be more or fewer channels 206.

Figure 17:
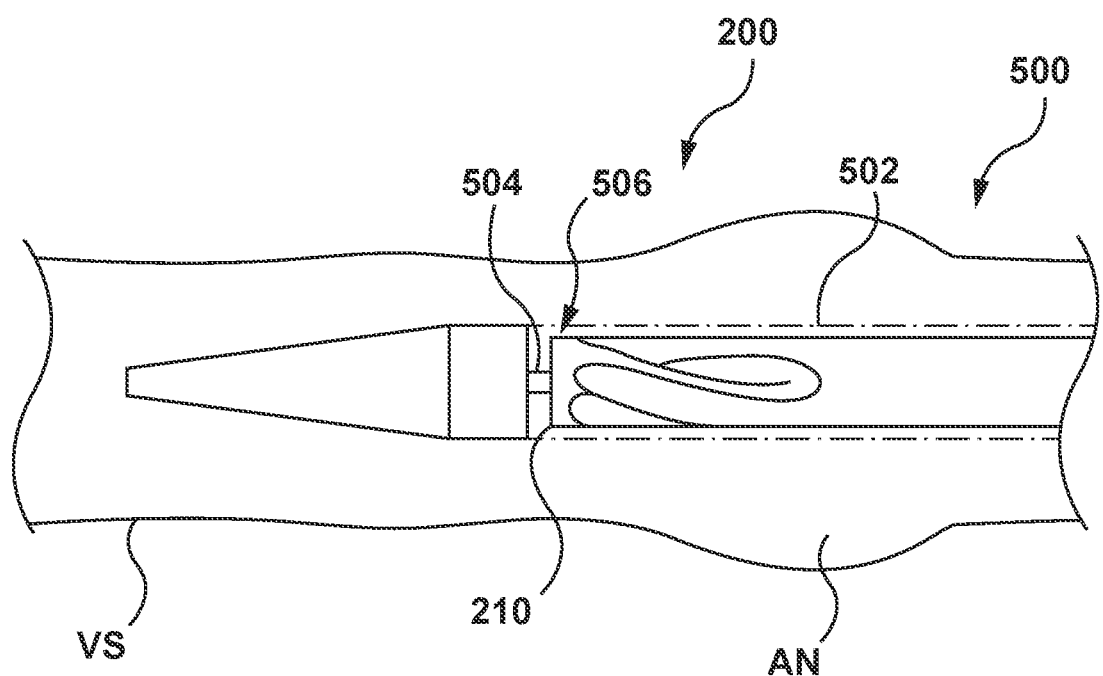
FIG. 17 depicts a side view of the stent-graft prosthesis of FIG. 13 in situ, wherein the stent-graft prosthesis is disposed on a distal portion of a delivery system and is in a radially compressed configuration.
Figure 18A:
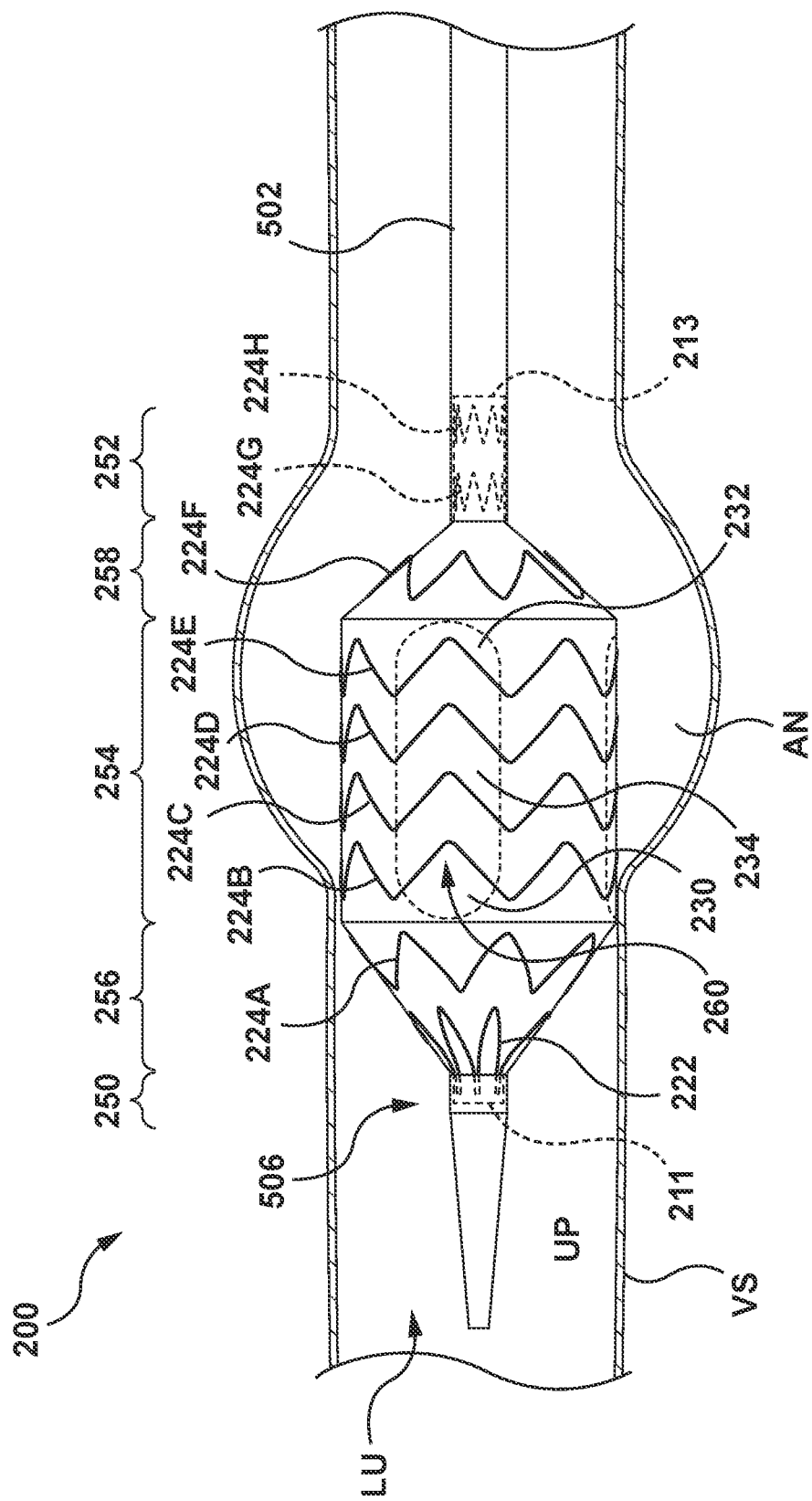
FIG. 18A depicts a side view of the stent-graft prosthesis of FIG. 13 in situ, wherein the stent-graft prosthesis is disposed at the distal portion of the delivery system and is in a partially expanded configuration.
Figure 18B:
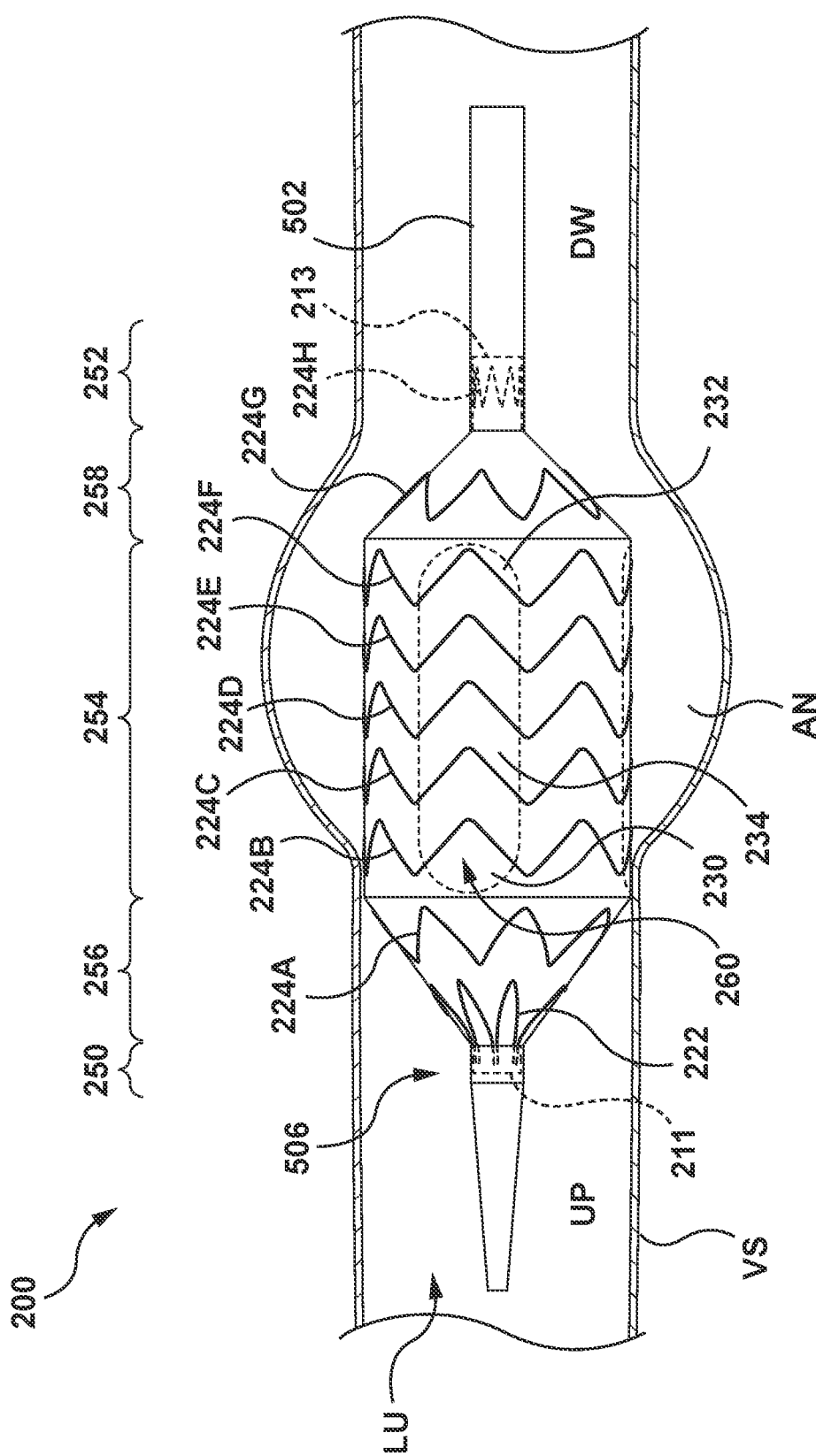
FIG. 18B depicts a side view of the stent-graft prosthesis of FIG. 13 in situ in a partially expanded configuration with the outer sheath retracted more than in FIG. 18A.
Figure 18C:
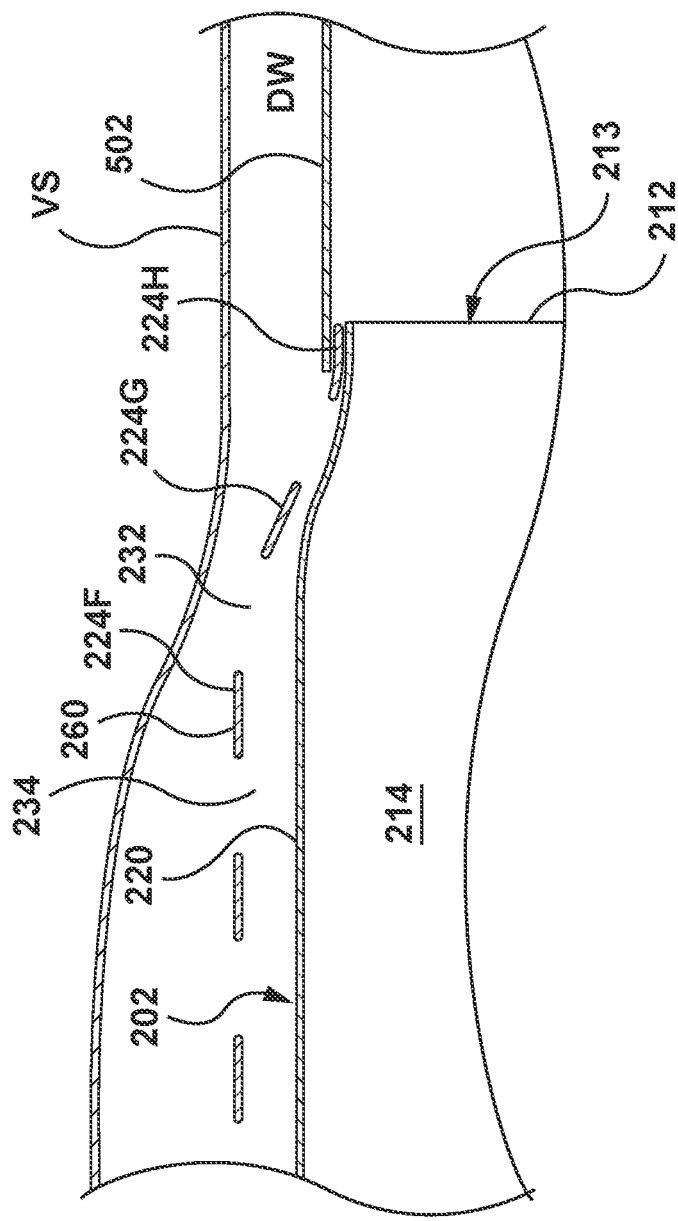
FIG. 18C depicts a partial cross-sectional view of a distal portion of the stent-graft prosthesis
Figure 19:
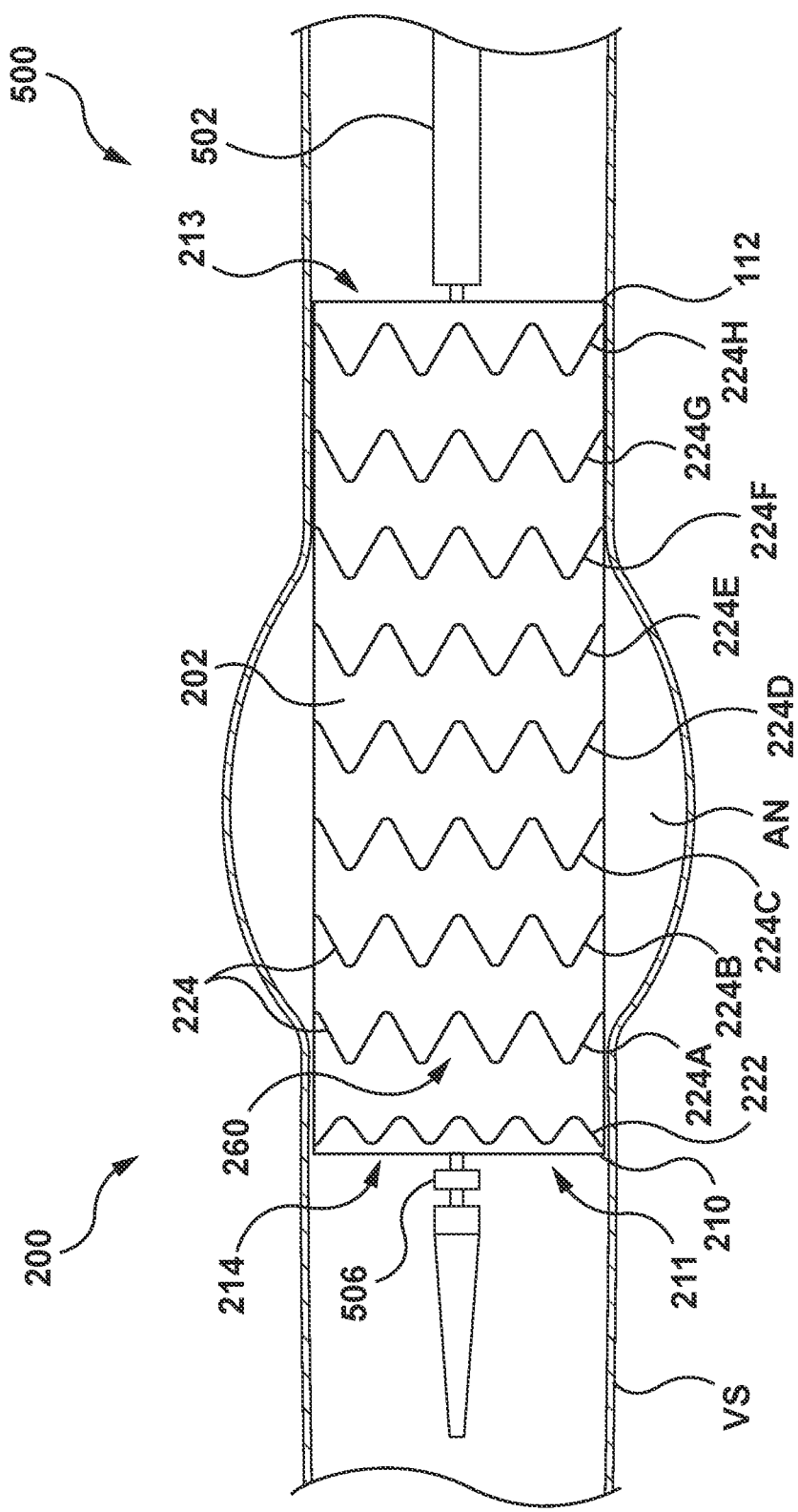
FIG. 19 depicts a side view of the stent-graft prosthesis of FIG. 13 in situ, wherein the stent-graft prosthesis is in a radially expanded configuration.

FIGS. 17-19, which are sectional cutaway views of a vessel illustrating the delivery, positioning and deployment of the stent-graft prosthesis 200 at the site of a vessel abnormality, will be referenced to explain the operation of the stent-graft prosthesis 200. While the vessel abnormality of FIGS. 17-19 is an aneurysm, it will be understood that this is by way of example and not limitation and embodiments of the stent-graft prosthesis 200 may be utilized with other vessel abnormalities including, but not limited to dissections and transections.

Referring now to FIG. 17, a distal portion of a delivery system 500 is shown with the stent-graft prosthesis 200 disposed in a radially compressed configuration thereon. The stent-graft 200 has been advanced to a desired treatment site of a vessel VS, which in this example is the location of an aneurysm AN. The delivery system 500 includes at least an outer sheath 502 and an inner shaft 504 having a tip capture mechanism 506 mounted thereon. The first end 211 of the stent-graft prosthesis 200 is releasably coupled to the tip capture mechanism 506. The stent-graft prosthesis 200 is mounted on the inner shaft 504 and the outer sheath 502 encapsulates, covers, or restrains the stent-graft prosthesis 200 in the radially compressed configuration for delivery thereof. In embodiments hereof, the delivery system 500 may be similar to the Captiva Delivery System, manufactured by Medtronic Vascular, Inc. of Santa Rosa, California, or as a delivery system as described in U.S. Patent Application Publication No. 2009/0276027 to Glynn, or U.S. Pat. No. 8,882,828 to Kinkade et al., previously incorporated by reference in their entirety.

Once the stent-graft prosthesis 200 is at the desired treatment location within the vessel VS, the stent-graft prosthesis 200 may be deployed from the delivery system 500. The outer sheath 502 of the delivery system 500 is retracted to release a portion of the stent-graft prosthesis 200. The released portion of the stent-graft prosthesis 200 radially expands within the vessel VS and the stent-graft prosthesis 200 transitions to the partially expanded configuration. As shown in FIG. 18A, a first or tip-capture portion 250 of the stent-graft prosthesis 200, including at least the first end 211, is restrained in the radially compressed state by the tip-capture mechanism 506. A second or distal restrained portion 252 is restrained in the radially compressed state by the outer sheath 502. At the deployment moment shown in FIG. 18A, the distal restrained portion 252 includes the body stents 224G and 224H. A third or expanded portion 254 of the stent-graft prosthesis 200 expands to the radially expanded state to conformingly engage an inner wall of the vessel VS. In FIG. 18A, the expanded portion 254 includes the body stents 224B-224F. A fourth or tapered inlet portion 256 is disposed between the tip-capture portion 250 and the expanded portion 254 and is held in the partially expanded state by the tip-capture portion 250 in the radially compressed state and the expanded portion 254 in the radially expanded state. In the embodiment shown, the tapered inlet portion 256 includes the body stent 224A. A fifth or tapered outlet portion 258 is disposed between the expanded portion 254 and the distal restrained portion 252, and is held in the partially expanded state by the expanded portion 254 in the radially expanded state and the distal restrained portion 252 in the radially compressed state. In the state of deployment shown in FIG. 18A, the tapered outlet portion 258 includes the body stent 224F, but this varies as the stent-graft prosthesis 200 is being deployed, as explained in more detail below.

The lumen LU of the vessel VS is generally occluded when the stent-graft prosthesis 200 is in the partially expanded configuration and disposed therein. Thus, as can be seen in FIG. 18A, absent the channel entrances 230, blood pressure against the stent-graft prosthesis 200 may cause the stent-graft prosthesis 200 to move during deployment. However, when in the partially expanded configuration of FIG. 18A, blood flow is enabled through the channels 206. In particular, as explained above, the channel entrances 230 are disposed in the tapered inlet portion 256 of the partially deployed stent-graft prosthesis 200. In this partially expanded state of the tapered inlet portion 256, the blood flows along the exterior surface 220 of the graft material 202 where the graft material 202 is attached to the body stent 224A. As the blood flows past the body stent 224A, the graft material 202 is not attached to the first segments of the body stent 224B. Thus, the blood flow forces the graft material 202 radially inward away from the first segments 260 of the body stent 224B, thereby creating the channel entrances 230 and enabling blood flow into the channel lumen 234. Similarly, the tapered outlet portion 258 is in the partially expanded state. Therefore, the channel exits 232 are disposed at the tapered outlet portion 258. In particular, the channel exits 232 are formed between the most distal body stent 224 of the expanded portion 254 and the most proximal body stent 224 of the tapered outlet portion 258. Thus, in the embodiment shown in FIG. 18A, the channel exits 232 are formed between the body stent 224E and the body stent 224F, as shown. The channel exits 232 are formed at this location because the graft material 202 at the first segments 260 of the body stent 224E hangs below the body stent 224E. However, because the body stent 224F is only partially expanded, the graft material 202 at the body stent 224F is adjacent the body stent 224F. Thus, any blood flow in the channel lumen 234 escapes the channel lumen 234 and a channel exit 232 is formed. FIG. 18C is a partial cross-sectional view of a portion of FIG. 18A showing this feature.

Thus, blood from an upstream side UP of the stent-graft prosthesis 200 is permitted to travel through each channel 206 to the downstream side DW of the stent-graft prosthesis 200. More precisely, blood on the upstream side UP of the stent-graft prosthesis 200 pushes the graft material 202 radially inward, away from the uncoupled portions of the body stents 224, thereby opening each channel 206. Blood flow enlarges each channel 206 when the stent-graft prosthesis 200 is in the partially expanded configuration. Blood enters each channel 206 through the corresponding channel entrance 230, flows through the channel lumen 234 outside of the outer surface 220 of the graft material 202. Radially outside of the outer surface 220 of the graft material at the channel lumens 234 are the respective first segment 260 of the each body stent 224 and the adjacent wall of the vessel VS. Thus the channels 234 are formed between the outer surface 220 of the graft material 202 and the first segment 260 of each body stent 224 in the radially expanded state/the adjacent wall of the vessel VS. The blood exits to the downstream side DW of the stent-graft prosthesis 200 through the corresponding channel exit 232. The flow of blood through the channel 206 from the upstream side UP to the downstream side DW of the stent-graft prosthesis 200 relieves pressure associated with pulsatile blood flow on the upstream side UP of the stent-graft prosthesis 200. More specifically, when the stent-graft 200 is in the partially expanded configuration, the channels 206 relieve upstream pressure against the outer surface 220 of the graft material 202 at the tapered inlet portion 256. When the pressure associated with the pulsatile blood flow is relieved on the upstream side UP by the channel 206 during deployment of the stent-graft prosthesis 200, the stent-graft prosthesis 200 can be more accurately positioned and easily maintained during deployment.

It will be understood that as the outer sheath 502 is retracted, the body stents 224 are sequentially released and the number of body stents 224 of the third portion 254 increases. With the channel exit 232 of each channel 206 being defined by the body stent 224 in the radially expanded state nearest the second end 213, which is a part of the expanded portion 254, the channel exit 232 for each channel 206 effectively moves longitudinally toward the second end 212 as the stent-graft 200 is deployed. For example, FIG. 18B shows the outer sheath 502 further retracted as compared to FIG. 18A. Thus, in FIG. 18B, the body stent 224F has expanded from the partially expanded state in the tapered outlet portion 258 to the expanded stated in the expanded portion 254. Further, the body stent 224G has been released from the outer sheath 502 and has transitioned from the radially compressed state of the distal restrained portion 252 to the partially expanded state of the distal outlet portion 258. Thus, the channel exits 232 have moved towards the second end 213 of the stent-graft prosthesis 200, as shown in FIG. 18B.

When final deployment of the stent-graft prosthesis 200 is desired, the outer sheath 502 is retracted to release the second end 213 of the stent-graft prosthesis 200, thereby enabling the second end 213 to radially expand to the radially expanded configuration. Further, the tip capture mechanism 506 is actuated to release the first end 211 of the stent-graft prosthesis 200 such that the first end 211 expands to the radially expanded configuration. With both the first and second ends 211, 213 expanded, the stent-graft prosthesis 200 is in the radially expanded configuration within the vessel VS, as shown in FIG. 19. The full retraction of the sheath 502 and release of the first end 211 from the tip-capture mechanism 506 may simultaneously or sequentially. When the first end 211 of the stent-graft prosthesis 211 is released from the tip-capture mechanism 506, the seal stent 222 and the body stent 224A expand to the radially expanded configuration. When in the radially expanded configuration, the seal stent 220 conformingly seals to the wall of the vessel VS, preventing blood flow between the graft material 202 and the wall of the vessel VS. Because both the seal stent 222 and the body stent 224A do not have first segments 260 with the graft material 202 uncoupled thereto, blood is blocked from entering the channel entrances adjacent the body stent 224B. Similarly, because the body stent 224H does not have first segments 260 with the graft material 202 uncoupled thereto, the channel exits 236 adjacent the body stent 224G are closed. Further, when the stent-graft 200 is in the radially expanded configuration, blood flows from the first end 210, through the graft lumen 214, and exits through the second end 212. Blood flow through the graft lumen 214 forces the graft material 202 radially outward against first segments 260 of the body stents 224 and the wall of the vessel VS, collapsing the channels 206 (not visible in FIG. 19).

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method comprising:
    delivering a stent-graft prosthesis to a treatment site of an aneurysm in a vessel such that an upstream portion of the stent-graft is disposed upstream of the aneurysm, the stent-graft prosthesis including graft material and a frame, the graft material defining a central lumen having an upstream end and a downstream end;
    partially deploying the stent-graft prosthesis to a partially deployed configuration such that at least a portion of the upstream portion of the stent-graft prosthesis upstream of the aneurysm is radially expanded against an inner wall of the vessel and blood cannot exit the downstream end of the central lumen, wherein the stent-graft prosthesis includes a channel exit downstream of the upstream portion, upstream of the downstream end of the channel lumen, and disposed within the aneurysm such that blood flow within the central lumen exits through the channel exit with the stent-graft prosthesis in the partially deployed configuration;
    fully deploying the stent-graft prosthesis such that the upstream portion of the stent-graft prosthesis upstream of the aneurysm is radially expanded against the inner wall of the vessel, a downstream portion of the stent-graft prosthesis is radially expanded against the inner wall of the vessel, the channel exit disposed within the aneurysm is closed such that blood flow from the central lumen is prevented from exiting the central lumen through the channel exit, the downstream end of the central lumen is open, and blood flow through the central lumen exits the central lumen through the downstream end of the central lumen.

2. The method of claim 1, wherein the stent-graft prosthesis further includes a channel entrance in the upstream portion downstream of the upstream end of the stent-graft prosthesis such that in the partially deployed configuration blood enters the central lumen through the channel entrance.

3. The method of claim 2, wherein fully deploying the stent-graft prosthesis comprises closing the channel entrance.

4. The method of claim 3, wherein the channel entrance includes a valve assembly, wherein in the partially deployed configuration the valve assembly is in an open state, wherein closing the channel entrance comprises closing the valve assembly to prevent blood from entering the central lumen through the channel entrance.

5. The method of claim 1, wherein the channel exit includes a valve assembly, wherein in the partially deployed configuration the valve assembly is in an open state, wherein fully deploying the stent-graft prosthesis includes closing the valve assembly to prevent blood from exiting the central lumen through the channel exit.

6. A method comprising:
delivering a stent-graft prosthesis to a treatment site in a vessel such at an upstream portion of the stent-graft is disposed upstream of the treatment site, the stent-graft prosthesis including graft material and a frame, the graft material defining a central lumen having an upstream end and a downstream end;
partially deploying the stent-graft prosthesis to a partially deployed configuration such that at least a portion of the upstream portion of the stent-graft prosthesis upstream of the treatment site is radially expanded against an inner wall of the vessel and blood cannot exit the downstream end of the central lumen, wherein a channel is formed downstream of the upstream end of the central lumen and between an outer surface of the graft material and an adjacent first segment of the frame to which the graft material is not attached such that the blood flows past the stent-graft outside of the graft material when the stent-graft prosthesis is in a partially expanded configuration, and fully deploying the stent-graft prosthesis such that the upstream portion of the stent-graft prosthesis upstream of the channel is radially expanded against the inner wall of the vessel to block access to the channel, the downstream end of the central lumen is open, and blood flow through the central lumen exits the central lumen through the downstream end of the central lumen.

7. The method of claim 6, frame includes a plurality of first segments aligned longitudinally such that the channel is formed between the first segments and the outer surface of the graft material to which the graft material is not attached such that the graft material is spaced from the first segments.

8. The method of claim 6, wherein fully deploying the stent-graft prosthesis to block access to the channel comprises radially expanding the frame upstream of the channel, wherein the frame upstream of the channel does not include a segment unattached to the graft material that enables blood flow between the outer surface of the graft material and the frame.

9. The method of claim 8, wherein fully deploying the stent-graft prosthesis comprises blocking an exit from the channel downstream of the upstream portion of the stent-graft prosthesis, wherein the frame downstream of the channel does not include a segment unattached to the graft material that enables blood flow between the outer surface of the graft material and the frame.

* * * * *